United States Patent
Kozwich et al.

(12) 
(10) Patent No.: US 6,649,378 B1
(45) Date of Patent: Nov. 18, 2003

(54) SELF-CONTAINED DEVICE INTEGRATING NUCLEIC ACID EXTRACTION, AMPLIFICATION AND DETECTION

(75) Inventors: Diane L. Kozwich, Englewood, CO (US); John C. Gerdes, Denver, CO (US)

(73) Assignee: Xtrana, Inc., Broomfield, CO (US)

( * ) Notice: Subject to any disclaimer, the term of this patent is extended or adjusted under 35 U.S.C. 154(b) by 129 days.

(21) Appl. No.: 09/705,043

(22) Filed: Nov. 2, 2000

Related U.S. Application Data

(63) Continuation of application No. 09/141,401, filed on Aug. 27, 1998, now Pat. No. 6,153,425, which is a continuation-in-part of application No. 09/061,757, filed on Apr. 16, 1998, which is a continuation-in-part of application No. 08/679,522, filed on Jul. 12, 1996, now Pat. No. 5,955,351.
(60) Provisional application No. 60/000,885, filed on Jul. 13, 1995, and provisional application No. 60/041,999, filed on Apr. 16, 1997.

(51) Int. Cl.[7] .......................... C12P 19/34; C12M 1/34; C07H 21/04; G01N 30/96; G01N 30/02
(52) U.S. Cl. .......................... 435/91.2; 435/6; 435/91.1; 435/287.2; 422/68.1; 422/69; 422/70; 536/23.1; 536/24.3; 536/24.31; 536/24.33
(58) Field of Search .......................... 435/6, 91.1, 91.2, 435/183, 287.2; 536/23.1, 24.3, 24.31, 24.37; 475/287.2; 422/68.1, 69, 70

(56) References Cited

U.S. PATENT DOCUMENTS

| | | | |
|---|---|---|---|
| 5,116,576 A | | 5/1992 | Stanley .................... 422/61 |
| 5,141,850 A | | 8/1992 | Cole et al. ................ 436/525 |
| 5,230,864 A | | 7/1993 | Columbus ................. 422/100 |
| 5,244,635 A | | 9/1993 | Rabson et al. ............. 422/72 |
| 5,273,882 A | * | 12/1993 | Snitman et al. ............ 435/6 |
| 5,310,650 A | | 5/1994 | McMahon et al. .......... 435/6 |
| 5,415,839 A | | 5/1995 | Zaun et al. ................ 422/64 |
| 5,527,673 A | * | 6/1996 | Reinhartz et al. ........... 435/6 |
| 5,639,428 A | | 6/1997 | Cottingham ............... 422/112 |
| 5,714,380 A | | 2/1998 | Neri et al. ................. 435/287 |
| 5,830,664 A | * | 11/1998 | Rosemeyer et al. ......... 435/6 |
| 5,955,351 A | * | 9/1999 | Gerdes et al. ............. 435/287.2 |
| 5,989,813 A | * | 11/1999 | Gerdes ...................... 435/6 |
| 6,153,425 A | * | 11/2000 | Kozwich et al. ........ 435/287.2 |

* cited by examiner

*Primary Examiner*—B. L. Sisson
(74) *Attorney, Agent, or Firm*—Steven C. Petersen; Sarah S. O'Rourke; Hogan & Hartson LLP

(57) ABSTRACT

Self-contained devices are described that integrate nucleic acid extraction, specific target amplification and detection into a single device. This integration permits rapid and accurate nucleic acid sequence detection. The invention may be used, for example, in the screening for nucleic acid sequences which may be indicative of genetic defects or contagious diseases, as well as for monitoring efficacy in the treatment of contagious diseases.

16 Claims, 19 Drawing Sheets

$10^{10}$  $10^9$  $10^8$  $10^7$  $10^6$

SEQUENCE LISTING

<160> NUMBER OF SEQ ID NOS: 13

<210> SEQ ID NO 1
<211> LENGTH: 52
<212> TYPE: DNA
<213> ORGANISM: artificial sequence
<220> FEATURE:
<223> OTHER INFORMATION: primer

<400> SEQUENCE: 1
aattctaata cgactcacta tagggtgcta tgtcacttcc ccttggttct ct        52

<210> SEQ ID NO 2
<211> LENGTH: 29
<212> TYPE: DNA
<213> ORGANISM: artificial sequence
<220> FEATURE:
<223> OTHER INFORMATION: primer

<400> SEQUENCE: 2
agtgggggga catcaagcag ccatgcaaa                                  29

<210> SEQ ID NO 3
<211> LENGTH: 20
<212> TYPE: DNA
<213> ORGANISM: artificial sequence
<220> FEATURE:
<223> OTHER INFORMATION: capture probe

<400> SEQUENCE: 3
tggcctggtg caataggccc                                            20

<210> SEQ ID NO 4
<211> LENGTH: 20
<212> TYPE: DNA
<213> ORGANISM: artificial sequence
<220> FEATURE:
<223> OTHER INFORMATION: capture probe

<400> SEQUENCE: 4
cccattctgc agcttcctca                                            20

<210> SEQ ID NO 5
<211> LENGTH: 15
<212> TYPE: DNA
<213> ORGANISM: artificial sequence
<220> FEATURE:
<223> OTHER INFORMATION: primer

<400> SEQUENCE: 5
cgatcgagca agcca                                                 15

<210> SEQ ID NO 6
<211> LENGTH: 15
<212> TYPE: DNA
<213> ORGANISM: Artificial Sequence
<220> FEATURE:
<223> OTHER INFORMATION: primer

<400> SEQUENCE: 6
cgagccgctc gctga                                                 15

<210> SEQ ID NO 7
<211> LENGTH: 40

```
<212> TYPE: DNA
<213> ORGANISM: artificial sequence
<220> FEATURE:
<223> OTHER INFORMATION: primer

<400> SEQUENCE: 7
accgcatcga atgcatgtct cgggtaaggc gtactcgacc                              40

<210> SEQ ID NO 8
<211> LENGTH: 40
<212> TYPE: DNA
<213> ORGANISM: artificial sequence
<220> FEATURE:
<223> OTHER INFORMATION: primer

<400> SEQUENCE: 8
cgattccgct ccagacttct cgggtgtact gagatcccct                              40

<210> SEQ ID NO 9
<211> LENGTH: 91
<212> TYPE: DNA
<213> ORGANISM: Mycobacterium tuberculosis

<400> SEQUENCE: 9
tggacccgcc aacaagaagg cgtactcgac ctgaaagacg ttatccacca tacggatagg        60
ggatctcagt acacatcgat ccggttcagc g                                       91

<210> SEQ ID NO 10
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<223> OTHER INFORMATION: residues 9-12 are ribonucleoside bases

<400> SEQUENCE: 10
aaagatgtag agggtacaga                                                    20

<210> SEQ ID NO 11
<211> LENGTH: 24
<212> TYPE: DNA
<213> ORGANISM: artificial sequence
<220> FEATURE:
<223> OTHER INFORMATION: synthetic target

<400> SEQUENCE: 11
aatctgtacc ctctacatct ttaa                                               24

<210> SEQ ID NO 12
<211> LENGTH: 28
<212> TYPE: DNA
<213> ORGANISM: artificial sequence
<220> FEATURE:
<223> OTHER INFORMATION: primer

<400> SEQUENCE: 12
ataatccacc tatcccagta ggagaaat                                           28

<210> SEQ ID NO 13
<211> LENGTH: 28
<212> TYPE: DNA
```

-continued

```
<213> ORGANISM: artificial sequence
<220> FEATURE:
<223> OTHER INFORMATION: primer

<400> SEQUENCE: 13
tttggtcctt gtcttatgtc cagaatgc                                28
```

SELF-CONTAINED DEVICE INTEGRATING NUCLEIC ACID EXTRACTION, AMPLIFICATION AND DETECTION

RELATED APPLICATIONS

This application is a Continuation of U.S. patent application Ser. No. 09/141,401, filed Aug. 27, 1998, now issued as U.S. Pat. No. 6,153,425, which is a Continuation-in-Part of U.S. patent application Ser. No. 08/679,522, filed Jul. 12, 1996, now issued as U.S. Pat. No. 5,955,351, which claims priority to Provisional Patent Application Serial No. 60/000,885, filed Jul. 13, 1995, now abandoned; this application is also a Continuation-in-Part of U.S. patent application Ser. No. 09/061,757, filed Apr. 16, 1998, which claims priority to Provisional Patent Application Serial No. 60/041,999, filed Apr. 16, 1997, now abandoned. Applicants hereby claim the earliest filing date, Jul. 13, 1995, for the instant application.

BACKGROUND OF THE INVENTION

1. Field of the Invention

This invention relates to the general fields of molecular biology and medical science, and specifically to a method of extracting nucleic acid, amplifying specific target sequences, and detecting amplified nucleic acid sequences in a self-contained device. This application thus describes a self-contained device capable of rapid and accurate detection of target nucleic acid sequences.

2. Description of the State of the Art

The use of nucleic acid probe tests based on hybridization in routine clinical laboratory procedures is hindered by lack of sensitivity. The ability to amplify nucleic acids from clinical samples has greatly advanced nucleic acid probe technology, providing the sensitivity lacking in earlier versions of non-isotopic assays. Sensitivity afforded by oligonucleotide probe tests utilizing nucleic acid amplification now exceeds that of any other method. Nucleic acid amplification procedures can detect a single copy of a specific nucleic acid sequence. Routine detection and identification of specific gene sequences has extremely broad applications in a number of settings and industries.

The major barrier for the transfer of technology to routine field testing is the absence of an economical and easy-to-use system or apparatus. In order to compete in today's cost conscious environment, genetic based testing must provide for high throughput while incorporating adequate controls and safeguards to prevent false positive results due to sample cross-contamination.

Current technology involves several steps, although recent developments are directed toward automating systems for detection of the amplified target sequence. The first step, extraction of nucleic acids, is accomplished in a variety of ways, for example, phenol extraction, chaotropic reagent extraction, chromatographic purification such as purification on silica membranes (WO 95/01359, specifically incorporated herein) and ultracentrifugation (Maniatis, et al., *Molecular Cloning: A Laboratory Manual,* Cold Spring Harbor Laboratory, Cold Spring Harbor, N.Y. (1982) specifically incorporated herein by reference). Phenol is a well-established health hazard and requires special handling for waste removal. The extraction method is also tedious and labor intensive. Ultracentrifugation often requires the use of expensive and hazardous chemicals as well as the use of sophisticated and costly equipment. The process often requires long run times, sometimes involving one or more days of centrifugation. The easiest and fastest method is separation using chromatography purification.

The second step, the amplification of the target nucleic acid, employs a variety of enzymes known as polymerases and ligases. Polymerase chain reaction (PCR) is the most commonly used amplification technique. The general principles and conditions for amplification of nucleic acids using PCR are quite well known in the art, the details of which are provided in numerous references including U.S. Pat. No. 4,683,195, U.S. Pat. No. 4,683,202 and U.S. Pat. No. 4,965,188, all to Mullis, et al., and all of which are specifically incorporated herein by reference. Thus, the details of PCR technology are not included herein. Other approaches include ligase chain reaction, Qβ replicase, strand displacement assay (SDA), transcription mediated iso CR cycling probe technology, nucleic acid sequence-based amplification (NASBA) and cascade rolling circle amplification (CRCA).

A current protein detection technology for antigen-antibody assays involves the use of microparticles. Furthermore, a variety of microparticle strategies for dipstick detection in antigen-antibody assays are currently available, for example, a currently marketed at-home pregnancy test (U.S. Pat. No. 5,141,850 to Cole et al., specifically incorporated herein by reference). Such tests use dyed particles that form a visible line following a specific antigen-antibody reaction.

The third and final step, detection of amplified nucleic acid for clinical use relies largely on hybridization of the amplified product and detection with a probe labeled with a variety of enzymes and luminescent reagents. U.S. Pat. No. 5,374,524 to Miller, which is specifically incorporated herein by reference, describes a nucleic acid probe assay that combines nucleic acid amplification and solution hybridization using capture and reporter probes. These techniques require multiple reagents, several washing steps, and specialized equipment for detection of the target nucleic acid. Moreover, these techniques are labor intensive and require technicians with expertise in molecular biology.

The use of probes comprised of oligonucleotide sequences bound to microparticles is well known and illustrated in the prior art. The mechanism for attachment of oligonucleotides to microparticles in hybridization assays and for the purification of nucleic acids is also well known. European Patent No. 200133, which is specifically incorporated herein, describes the attachment of oligonucleotides to water-insoluble particles less than 50 micrometers in diameter used in hybridization assays for the capture of target nucleotides. U.S. Pat. No. 5,387,512 to Wu, which is specifically incorporated herein by reference, describes the use of oligonucleotide sequences covalently bound to microparticles as probes for capturing PCR amplified nucleic acids. U.S. Pat. No. 5,328,825 to Findlay, which is specifically incorporated herein by reference, also describes an oligonucleotide linked by way of a protein or carbohydrate to a water-insoluble particle. The oligonucleotide probe is covalently coupled to the microparticle or other solid support. The sensitivity and specificity of all of the above-reference patents is based on hybridization of the oligonucleotide probe to the target nucleic acid.

The use of incorporated non-radioactive labels into amplification reactions for the detection of nucleic acids is also well known in the art. Nucleic acids modified with biotin (U.S. Pat. No. 4,687,732 to Ward et al.; European Patent No. 063879; both of which are specifically incorporated herein by reference), digoxigenin (European Patent No. 173251, which is specifically incorporated herein) and other haptens have also been used. For example, U.S. Pat. No. 5,344,757 to Graf, which is specifically incorporated herein by reference, uses a nucleic acid probe containing at least one hapten as a label for hybridization with a complementary target nucleic acid bound to a solid membrane. The sensitivity and specificity of these assays is based on the incorporation of a single label in the amplification reaction which can be detected using an antibody specific to the label. The usual case involves an antibody conjugated to an enzyme. Furthermore, the addition of substrate generates a colorimetric or fluorescent change which can be detected with an instrument.

Still, the above-described approaches are labor intensive with many steps and washes; require special and costly equipment for the detection of the target nucleic acid; require trained staff; and take several hours to complete. Several patents have issued which deal with automation of the processes of amplification and subsequent detection of the amplicon. These patents use specialized equipment and are still based on the principle of hybridization and immunoassay technology. For example, European Patent No. 320308, which is specifically incorporated herein by reference, describes a system detecting target nucleic acids amplified by the ligase chain reaction.

Nucleic acid probe technology has developed rapidly in recent years as the scientific community has discovered its value for detection of various diseases, organisms or genetic abnormalities. Amplification techniques have provided the sensitivity to qualitatively determine the presence of even minute quantities of nucleic acid. The drawback to wide spread use of this technology is the possibility of cross contamination of samples since the test is so sensitive. The cost of nucleic acid based testing is high as it requires highly skilled technicians and sophisticated equipment. Automated approaches eliminate the need for specially trained personnel, however, the cost of the equipment is very high and the possibility of contamination still exists since many samples will be processed by the same equipment.

There is still a need, therefore, for a method and device which provides for the rapid and accurate detection of amplified nucleic acid sequences which significantly decreases the possibility of cross-contamination of samples while further being both simple and economical to use.

SUMMARY OF THE INVENTION

It is an object of the present invention to provide novel, self-contained devices that integrate nucleic acid extraction, specific target amplification and detection methodologies into a single device, permitting rapid and accurate nucleic acid sequence detection. The present invention is applicable to all nucleic acids and derivatives thereof.

It is a further object of the present invention to provide methods of detecting nucleic acids using the self-contained devices of this invention.

To achieve the foregoing and other objects and in accordance with the purposes of the present invention, as embodied and broadly described therein, one embodiment of a self-contained device of this invention comprises a first hollow elongated cylinder with a single closed end and a plurality of chambers therein, and a second hollow elongated cylinder positioned inside the first cylinder and capable of relative rotation. A sample which may contain the target nucleic acid is introduced into the second cylinder for extraction. The extracted nucleic acid binds to a solid phase contained in the second cylinder, and therefore is not eluted from the solid phase by the addition of wash buffer. Amplification and labeling takes place in the second cylinder. Finally, the labeled, amplified product is introduced into a detection chamber in the first cylinder, where it reacts with microparticles conjugated with receptor-specific ligands for detection of the target nucleic acid.

To further achieve the foregoing, and in accordance with the purposes of the present invention, as embodied and broadly described therein, another embodiment of the invention, the self-contained device comprises four separate chambers: an extraction chamber, a waste chamber, an amplification chamber, and a detection chamber. In this embodiment, the sample which may contain the target nucleic acid is extracted, amplified and detected in separate and sequential chambers.

To further achieve the foregoing, and in accordance with the purposes of the present invention, as embodied and broadly described therein, yet another embodiment of this invention comprises a self-contained device for the extraction, amplification and detection of nucleic acid sequences, which comprises a first cylinder or PCR tube having a matrix cylinder or tube disposed contiguously therein. This embodiment may have a reagent cell that is inserted on top of the matrix tube, or alternatively the reagents may be adhered directly to the interior of the matrix tube. A detection result stick is inserted through an aperture into the device after the completion of the reaction or reactions.

To further achieve the foregoing, and in accordance with the purposes of the present invention, as embodied and broadly described therein, the present invention provides a method of detecting nucleic acids using the self-contained devices of this invention. In one embodiment, the amplification methodologies used in the self-contained devices of this invention produce bifunctionally labeled nucleic acids comprising two different labels. In another embodiment, the amplification methodology produces non-labeled nucleic acid which hybridizes to a bifunctionally labeled probe. In yet another embodiment, the amplification methodology produces a singly labeled nucleic acid which hybridizes to a singly labeled probe. The detection method used in the self-contained devices relies on microparticle detection technology, wherein receptors on the microparticles bind to a label on the nucleic acid or probe.

Other features and advantages of the present invention will become apparent from the following detailed description, taken in conjunction with the accompanying figures, that illustrate by way of example, the principles of the instant invention.

BRIEF DESCRIPTION OF THE FIGURES

The file of this patent contains at least one drawing executed in color. Copies of this patent with color drawings will be provided by the Patent and Trademark Office upon request and payment of the necessary fee.

REFERENCE NUMERALS IN DRAWINGS

Figure 1:
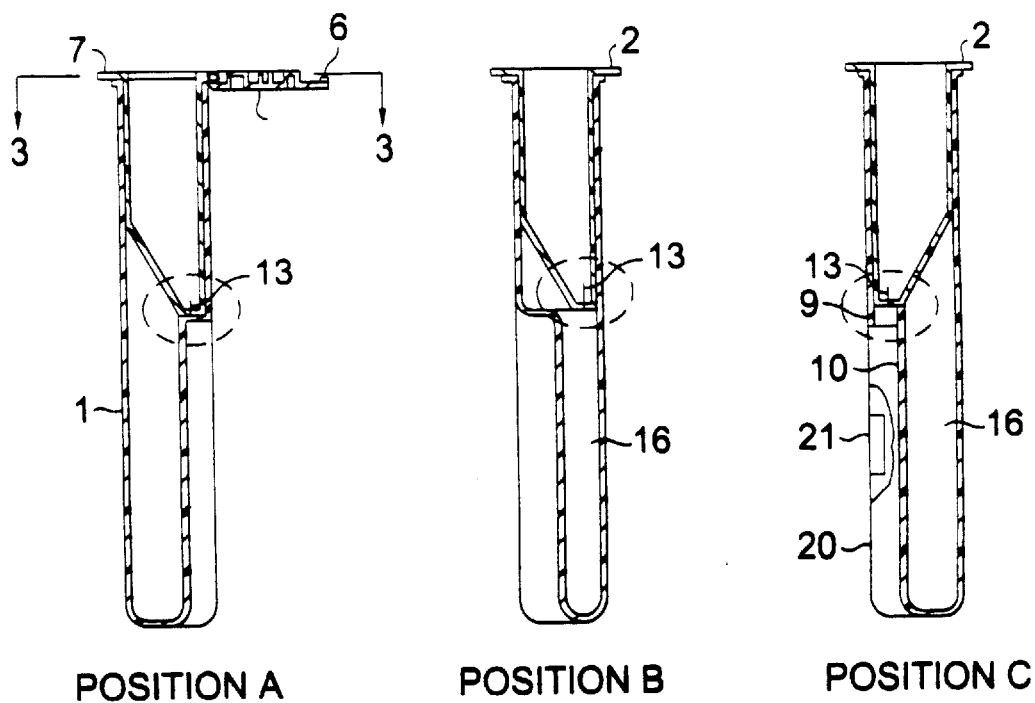
FIG. 1 is a perspective view of a self-contained device integrating nucleic acid extraction, amplification and detection, illustrating each of the three device rotational positions: A) closed; B) open; and C) elute.

| 1 | First hollow elongated cylinder |
| 2 | Second hollow elongated cylinder |
| 6 | Index pin |
| 7 | Index notch |
| 7' | Index notch |
| 7" | Index notch |
| 9 | Absorbent pad |
| 10 | Membrane Strip |
| 11 | Reaction bead |
| 12 | Reaction bead chamber |
| 13 | Aperture |
| 15 | Sealing lip |
| 16 | Reservoir |
| 17 | Solid surface |
| 18 | Knife-edge |
| 19 | Foil or foil/polymer membrane |
| 20 | Detection chamber |
| 21 | Transparent viewing window |
| 22 | Solid phase |
| 24 | Colored microparticles |
| 25 | Capture zone for target sequence |
| 26 | Capture zone for control sequence |
| 27 | Reagent cell |
| 28 | Pouch |
| 29 | Reagent |
| 30 | Liquid |
| 31 | Upper seal |
| 32 | Middle seal |
| 33 | Lower Seal |
| 34 | Upper screen |
| 35 | Lower screen |
| 36 | Solid phase matrix |
| 37 | Matrix tube |
| 38 | Locking/sealing means |
| 39 | Absorbent sample pad |
| 40 | Waste pad |
| 41 | Transparent body |
| 42 | Seal |
| 43 | PCR tube |
| 44 | Control indicator |
| 45 | Detection indicator |
| 46 | Result stick |
| 47 | Foil patch |
| 48 | Cap |
| 50 | Arrow |
| 58 | Porous membrane |
| 118 | Knife edge |

DETAILED DESCRIPTION OF THE PREFERRED EMBODIMENT

The present invention provides novel self-contained devices for detecting a target nucleic acid sequence that is present in a sample. The self-contained devices disclosed herein eliminate the possibility of cross-contamination from one sample to another by integrating nucleic acid extraction, amplification, and detection strategies in completely enclosed, disposable devices.

It will be recognized by those skilled in the art that assays for a broad range of target nucleic acid sequences that may be present in a sample may be performed in accordance with the present invention. Samples may include biological samples derived from agriculture sources, bacterial and viral sources, and from human or other animal sources, as well as other samples such as waste or drinking water, agricultural products, processed foodstuff, air, etc. Examples of biological samples include blood, stool, sputum, mucus, serum, urine, saliva, teardrop, tissues such as biopsy samples, histological tissue samples, and tissue culture products, agricultural products, waste or drinking water, foodstuff, air, etc. The present invention is useful for the detection of specific nucleic acid sequences corresponding to certain diseases or conditions such as genetic defects, as well as monitoring efficacy in the treatment of contagious diseases, but is not intended to be limited to these uses.

The following definitions will be helpful in understanding the specification and claims. The definitions provided herein should be borne in mind when these terms are used in the following examples and throughout the instant application.

As used herein, the term "target" nucleic acid molecule refers to the nucleic acid molecule that may be amplified or non-amplified for use with the presented methods. The "target" molecule can be purified, partially purified, or present in an unpurified state in the sample.

As used in this invention, the term "amplification" refers to a "template-dependent process" that results in an increase in the concentration of a nucleic acid sequence relative to its initial concentration. Preferred amplification methodologies for use in this invention include polymerase chain reaction (PCR), and isothermal reactions such as NASBA (U.S. Pat. No. 5,130,238, specifically incorporated herein) or strand displacement assay (SDA) (Walker, et al., *PNAS* 89:392, (1992) which is specifically incorporated herein by reference).

A "template-dependent process" is defined as a process that involves the "template-dependent extension" of a "primer" molecule. A "primer" molecule refers to a sequence of nucleic acid that is complementary to a portion of the target or control sequence and may or may not be labeled with a hapten. A "template dependent extension" refers to nucleic acid synthesis of RNA or DNA wherein the sequence of the newly synthesized strand of nucleic acid is dictated by the rules of complementary base pairing of the target nucleic acid and the primers.

In general, a self-contained device of this invention comprises a plurality of separate, sequential chambers, for example, an extraction chamber, a waste chamber, an amplification chamber, and a detection chamber, wherein a sample which may contain the target nucleic acid to be detected is extracted, amplified and detected in separate and sequential chambers. To use a multi-chambered self-contained device of this invention, a sample containing target nucleic acid and control nucleic acid is introduced into an extraction chamber for extraction of nucleic acid. The extraction chamber incorporates a nucleic acid extraction/solid phase nucleic acid binding protocol providing a rapid method of nucleic acid purification. The preferred extraction method makes use of chaotropic agents such as guanidine thiocyanate (GuSCN) to disrupt the cell membranes and extract the nucleic acid. Proteins are degraded by proteinases. The extracted nucleic acid binds to a solid phase membrane in the extraction chamber. The design of a fitting between the solid phase membrane and a seal located directly below the solid phase prevents waste from entering the amplification chamber.

In one embodiment, after the sample has been added to the extraction chamber, a supply assembly unit locks onto the top of a processor assembly unit by connecting a first and a second fitting. Following a 10–15 minute incubation allowing for nucleic acid extraction, the first of four plungers is depressed. Air in a compartment forces the extraction mixture past the solid phase membrane binding the nucleic acid. The filtrate is collected in a waste chamber. Depression of a second plunger forces a wash buffer stored in a wash buffer compartment across the solid phase membrane and filtrate passes to the waste chamber. The seal located directly below the solid phase membrane is disposed at an angle to aid in efficient collection of the waste. Depression of a third plunger forces air stored in a compartment across the solid phase membrane, insuring that all of the wash buffer is removed. The processor assembly unit twists, simultaneously breaking the seal and closing off a waste chamber conduit. Depression of a fourth plunger delivers an elution buffer stored in a compartment for elution of the nucleic acid from the solid phase and delivers a volume of nucleic acid into an amplification chamber.

The amplification chamber contains the reagents for amplification and hybridization. In an alternative embodiment, reagents for amplification and hybridization are in separate chambers. The amplification/hybridization process is characterized in that the sample is treated, after extraction, with two distinct labeled oligonucleotides primers. The sequence of the first primer is complementary to a partial sequence of the target nucleic acid and is labeled with hapten, for example, biotin. The sequence of the second primer is complementary to a partial sequence of the control nucleic acid and labeled with a second hapten, for example, digoxigenin. Either primer may contain a promoter region. Subjecting the mixture to amplification, preferably isothermal amplification, results in hapten labeled target nucleic acid sequences and hapten control nucleic acid sequences. The labeled, amplified nucleic acid sequences hybridize to oligonucleotides which are conjugated to microparticles of suitable color and diameter for detection. The microparticles are conjugated either with an oligonucleotide specific for binding a nucleic acid sequence on the target or with an oligonucleotide specific for binding a nucleic acid sequence on the control nucleic acid. The resulting microparticles, bound by hybridization to the amplicons, are detected in the detection chamber.

1. Three-chambered self-contained device

One embodiment of a self-contained device of the present invention, generally illustrated in FIG. 1, comprises a first hollow elongated cylinder with a single closed end and a plurality of chambers therein, and a second hollow elongated cylinder positioned contiguously inside the first cylinder and capable of relative rotation. In this embodiment, the extraction and amplification of nucleic acids take place in the second cylinder (the reaction chamber) of the self-contained device, detection takes place in a detection chamber of the first cylinder, and collection of waste occurs in a waste chamber of the first cylinder. The chambers of the self-contained device of FIG. 1 are functionally distinct, sequential and compact. The chambers deliver precise volumes, dispense reagents and collect waste. All of the steps of nucleic acid extraction, amplification and detection occur in the completely self-contained device with simple, fool-proof directions for use as described below.

Figure 2:
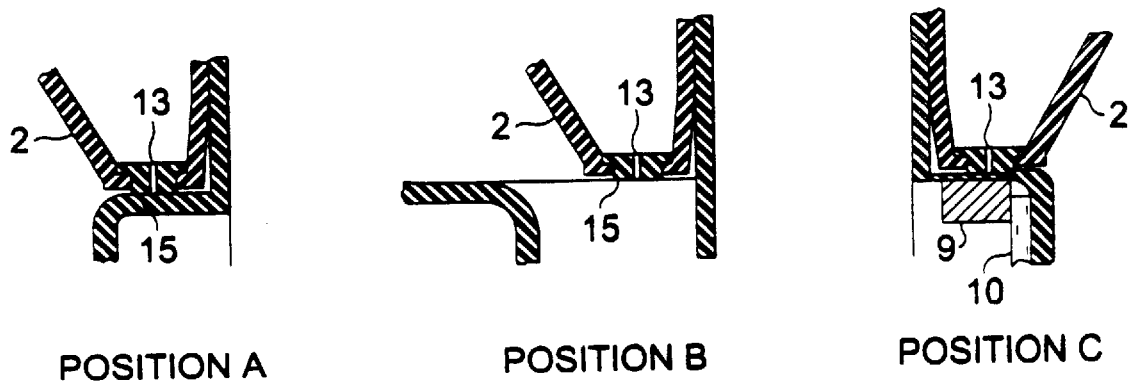
FIG. 2 is a schematic of the preferred sealing mechanism, illustrating each of the three device rotational positions: A) closed; B) open; and C) elute, which are enlargements of the encircled portions of positions A, B, and C as shown in FIG. 1.

With continued reference to FIG. 1, one embodiment of a self-contained device of this invention comprises a first hollow elongated cylinder 1 having one closed end and an integrally-molded cover 3 hinged to the opposing, opened end, and a second hollow elongated cylinder 2 that is positioned contiguously inside the first cylinder 1 and is capable of relative rotation. The preferred embodiment of the second cylinder 2 is a tapered cylinder terminating with an aperture 13 having a sealing lip 15 as shown in FIG. 2. The first cylinder 1 further consists of two chambers: a reservoir or waste chamber 16 and a detection chamber 20, the detection chamber further comprising a pad 9 and a strip 10. When sample is introduced into the device, nucleic acid extraction and amplification takes place in the second cylinder 2. The first hollow elongated cylinder 1 contains the detection chamber 20 having a means for detection and reservoir 16 for collecting the lysis buffer used in the extraction process and other buffers used in subsequent washes.

The second cylinder 2 rotates relative to the first cylinder 1 and locks into position A, position B or position C. At the tapered end of the second cylinder 2, an aperture 13 having a sealing lip 15 enables the second cylinder 2 to engage with either the detection chamber 20 or reservoir 16 of the first cylinder 1. The hinged cover 3 has one indexing pin 6 (shown in FIG. 1, position A) used for locking the second cylinder 2 in positions A, B and C. The second cylinder 2 contains three notches 7, 7' and 7" for indexing with the indexing pin 6 and locking the relative rotation of cylinders 1 and 2. The second cylinder 2 is closed to the reservoir 16 in the closed position A. In position A, the second cylinder 2 is sealed, allowing for the extraction step and the amplification step to take place. For purposes of illustration only, the method of using the self-contained device of FIG. 1 will be discussed with respect to amplification methods that produce bifunctionally labeled, amplified nucleic acids. However, it will be understood that other amplification methods, such as those that produce singly-labeled nucleic acids or unlabeled nucleic acids, may be used in the self-contained device of FIG. 1, as discussed below in detail. Thus, in one embodiment, the amplification produces a bifunctionally labeled target nucleic acid having a hapten A on one end and a hapten B on the other end of the amplified target nucleic acid. Amplification also produces a bifunctionally labeled control nucleic acid having a hapten C on one end and a hapten D on the other end.

In open position B, the second cylinder 2 is such that the opening 13 in the second cylinder 2 is not sealed and is over the reservoir 16. In open position B, the second cylinder 2 allows flow to the reservoir 16.

Figure 6:
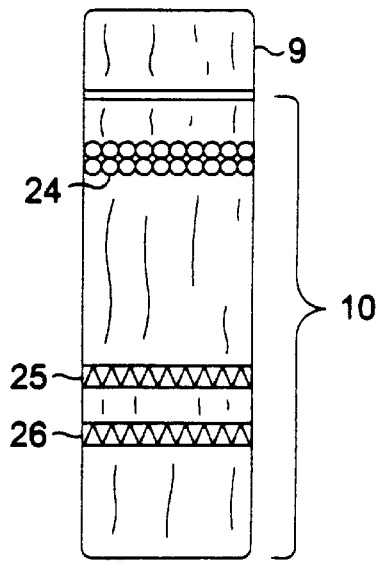
FIG. 6 depicts the relative position of the absorbent pad and membrane strip having microparticles and capture zones.

In elute position C, the second cylinder 2 is rotated such that the second cylinder 2 is not sealed and the opening 13 is over an absorbent pad 9 located in the detection chamber 20. In elute position C, amplified nucleic acid target and control are able to wick into the detection chamber 20. The absorbent pad 9 collects the amplified product and wicks the product onto a strip 10 of nylon, nitrocellulose or other suitable material. The strip 10 contains colored microparticles 24 and capture zones 25 and 26 for the target and the control sequences, respectively (FIG. 6). The detection chamber 20 contains a transparent viewing window 21 for observing the results of the reaction.

FIG. 2, which shows enlargements of the encircled portions of FIG. 1, illustrates the preferred embodiment of the sealing mechanism of the self-contained device of FIG. 1. In closed position A, the second cylinder 2 is sealed by a sealing lip 15 at the bottom of cylinder 2. The sealing lip 15 is composed of a flexible material that can be compressed when in contact with a solid surface 17 (FIG. 3) at the top of the first cylinder 1. With continued reference to FIG. 2, in open position B, rotation of the second cylinder 2 relative to the first cylinder 1 allows the contents of the second cylinder 2 to flow into the reservoir 16 through a solid phase 22 (FIG. 5), for example a porous membrane, in the bottom of the second cylinder 2. In this position, the sealing lip 15 is extended beyond the plane of compression and allows fluid to flow into the reservoir 16. The second cylinder 2 can also be rotated relative to the first cylinder 1 into elute position C. In this position, the sealing lip 15 is again extended beyond the plane of compression and allows amplified nucleic acid and control nucleic acid to wick onto an absorbent pad 9 and a strip 10 of membrane used for the detection step.

Figure 3:
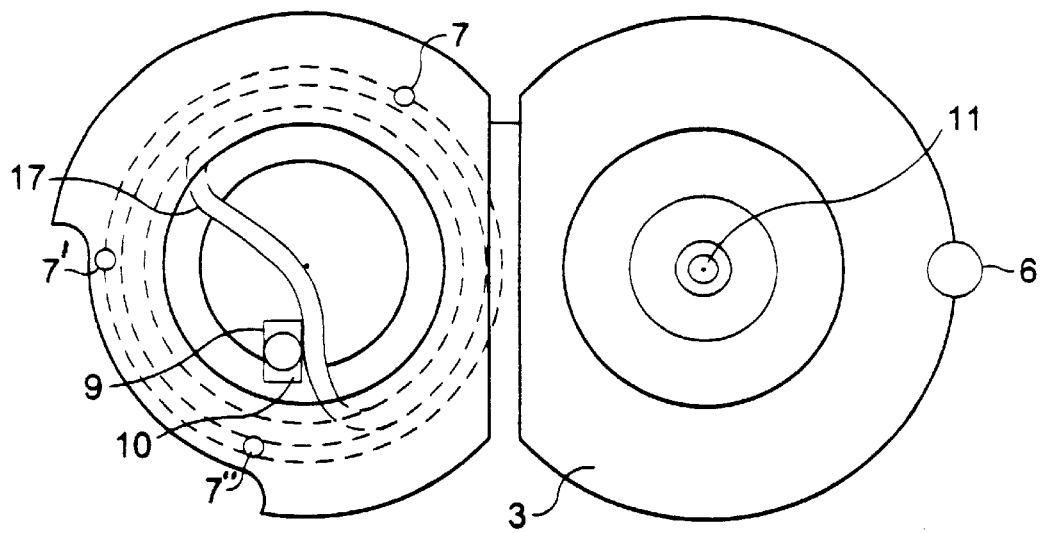
FIG. 3 is a top plan view of the device shown in FIG. 1, position A along line 3—3, showing the hinged cover in the open position.
Figure 4:
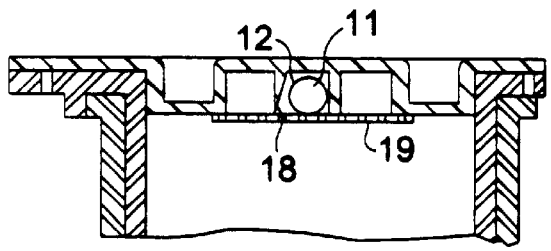
FIG. 4 is a side cross-sectional view of the hinged cover in the closed position and the reaction bead contained within a reaction bead chamber having an integral knife-edge.

A top plan view of the self-contained device of FIG. 1 and the hinged cover 3 in the open position is illustrated in FIG. 3. The index pin 6 is located on the hinged cover 3. Three index notches 7, 7', and 7" are located on the second cylinder 2. The hinged cover 3 contains a reaction bead 11 within a reaction bead chamber 12 (FIG. 4). This bead 11 contains the reaction enzymes and other reagents required for the amplification step. The hinged cover 3 may also contain a knife-edge 18, which when sufficient pressure is applied punctures a foil membrane 19 (FIG. 4), releasing the reaction bead 11 into the second cylinder 2.

Figure 5:
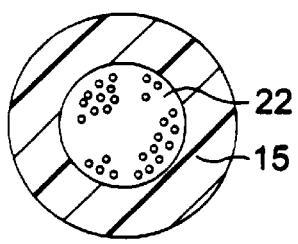
FIG. 5 is a top cross-sectional view of the aperture section of the second hollow elongated cylinder.

A cross-section of the bottom of the second cylinder 2 is illustrated in FIG. 5. The sealing lip 15 contains a solid phase 22 (e.g., a porous membrane) that binds the extracted nucleic acids or a solid phase 22 that holds a silica slurry (not shown) in the second cylinder 2.

As stated above, detection takes place in detection chamber 20. Preferably the detection method is a lateral flow assay. The specific reagents in the detection chamber will depend on the type of amplified product produced, that is whether the amplification produces a bifunctionally labeled, singly labeled, or unlabeled nucleic acid. In one embodiment, detection chamber 20 of the first cylinder 1 contains a pad 9 and a strip 10. FIG. 6 illustrates strip 10 containing a region with immobilized colored microparticles 24 and two capture zones 25 and 26. In this embodiment, the microparticles 24 are coated either with a receptor A' that is specific to hapten A the target nucleic acid, or with a receptor C' that is specific to hapten C on the control nucleic acid. Additionally, the target sequence capture zone 25 contains receptors B' that are specific for hapten B on the target sequence, and control sequence capture zone 26 contains receptors D' that are specific for hapten D on the control sequence.

Figure 7:
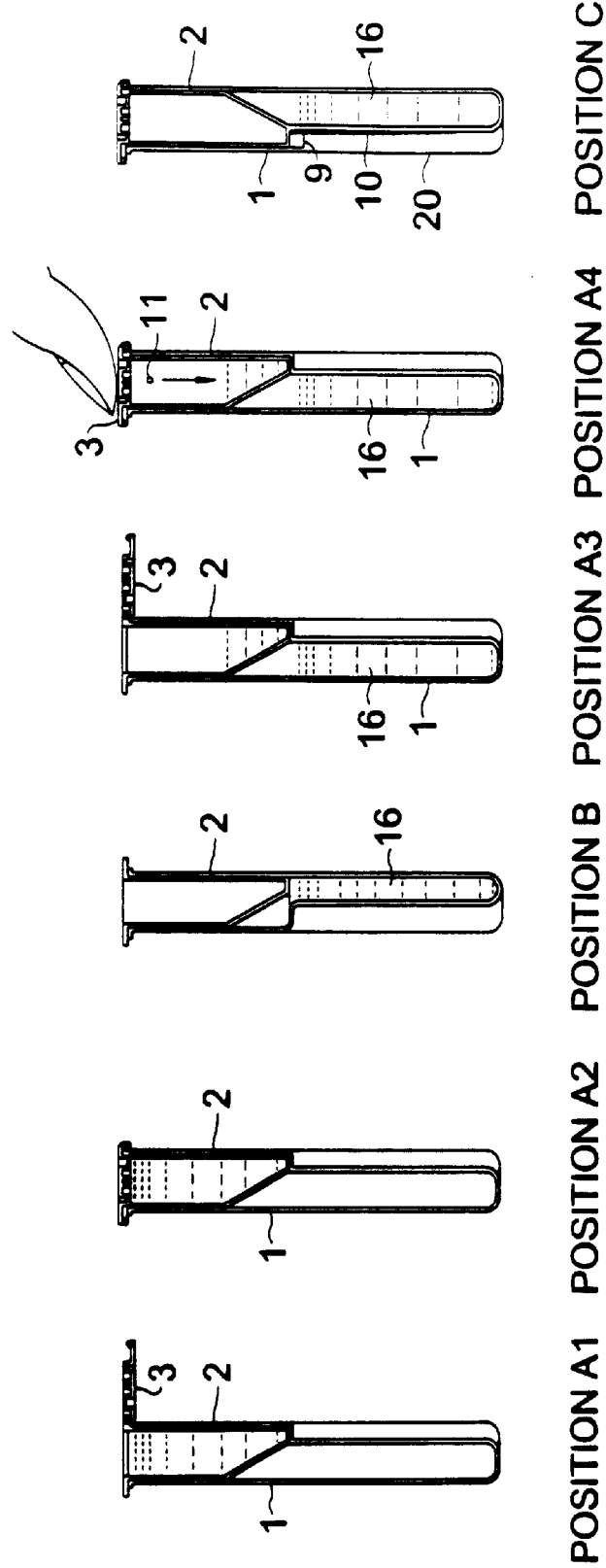
FIG. 7 depicts a sequential operating sequence of the self-contained device.

FIG. 7 depicts the sequence of steps for the extraction, amplification and detection of nucleic acid sequences using the embodiment of the self-contained device illustrated in FIG. 1. In the closed position A1, a sample containing a control nucleic acid and the target nucleic acid to be detected (if present) is introduced into the second cylinder 2. Preferably, second cylinder 2 has a capacity of 0.001 to 25 mL. The second cylinder 2 contains dry lysing reagents for extraction of nucleic acids. The sample provides the liquid that resuspends the lysing reagents. After a brief incubation period with the cover 3 closed (position A2), the second cylinder 2 is rotated into open position B. The extracted nucleic acid remains bound to the solid phase 22 or the silica slurry (not shown) in the second cylinder 2, while the liquid flows into the reservoir 16. In open position B, several washes with buffer or water follow.

Next, the second cylinder 2 is rotated into closed position A3 such that the second cylinder 2 is sealed. Water is added to the second cylinder 2 and the hinged cover 3 is closed (position A4). When sufficient pressure is applied to the hinged cover 3 as shown in position A4, foil membrane 19 is punctured by knife-edge 18 (FIG. 4), and the reaction bead 11 is released from the reaction bead chamber 12 into the second cylinder 2. The reaction bead 11 carries the enzymes necessary for amplification, which are resuspended in the water. Amplification takes place on the solid phase 22 (FIG. 5) or silica slurry (not shown) containing the bound, extracted nucleic acids and produces bifunctionally labeled amplified target nucleic acid labeled with haptens A and B, and bifunctionally labeled control nucleic acid labeled with haptens C and D.

After an appropriate incubation period, the second cylinder 2 is rotated relative to the first cylinder 1 into elute position C. The amplification reaction mixture is able to enter the detection chamber 20 as it is absorbed onto the pad 9. When the pad 9 absorbs a sufficient amount of liquid, the reaction mixture is wicked onto the membrane strip 10. On the membrane strip 10, receptors A' on colored microparticles 24 bind to haptens A on the amplified target, and receptors C' on microparticles 24 bind to haptens C on the control nucleic acids, and microparticle-bound nucleic acids travel to the capture zones 24 and 25 on the membrane strip 10. The target capture zone 25 contains receptors B' specific for haptens B on the target sequence, and control capture zone 26 contains receptors D' specific for haptens D on the control sequence. A visible line of detection forms at capture zone 25 if the target sequence is present and at capture zone 24 for the control sequence. The lines of detection are viewed from the transparent viewing window 21 (FIG. 1).

The bulk of the device shown in FIG. 1 is composed of a material that does not facilitate binding of nucleic acids and proteins. The preferred material is heat and cold resistant material which is light weight, rigid and sturdy. The preferred size is compact enough to fit into conventional size heat blocks, however, the size may be scaled up or down, accordingly. In a preferred embodiment, the self-contained device of FIG. 1 is inserted into a constant temperature environment such as a heat block, allowing the reactions to proceed at the preferred conditions of constant temperature.

2. Self-contained device comprising a matrix tube

Figure 16:
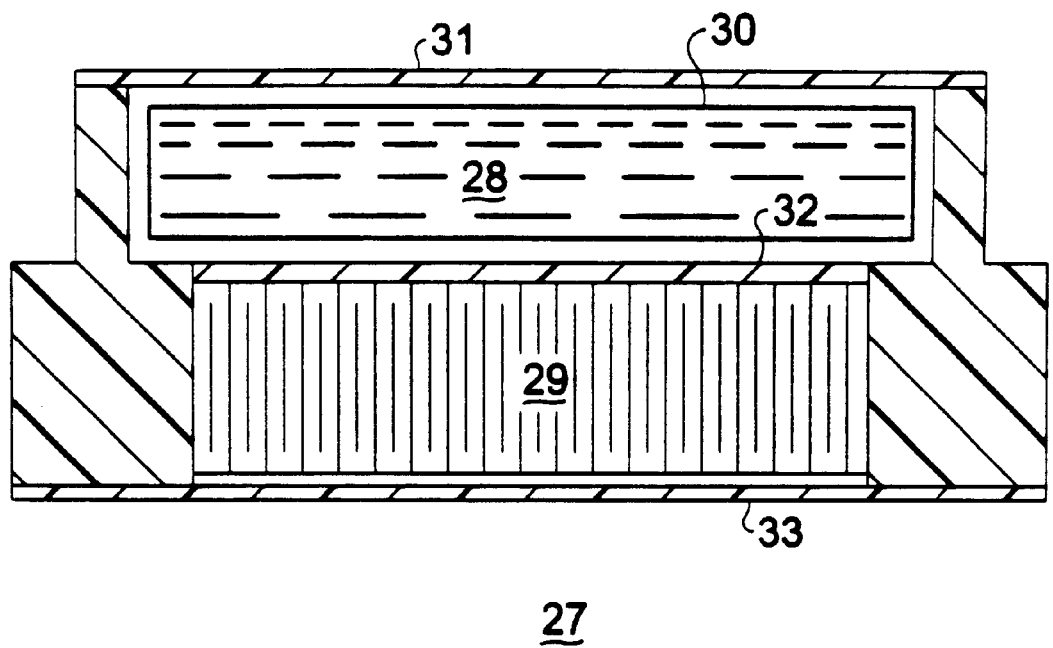
FIG. 16 depicts a side cross-sectional view of the reagent cell of an alternate embodiment of the invention, having a plurality of pouches.
Figure 19:
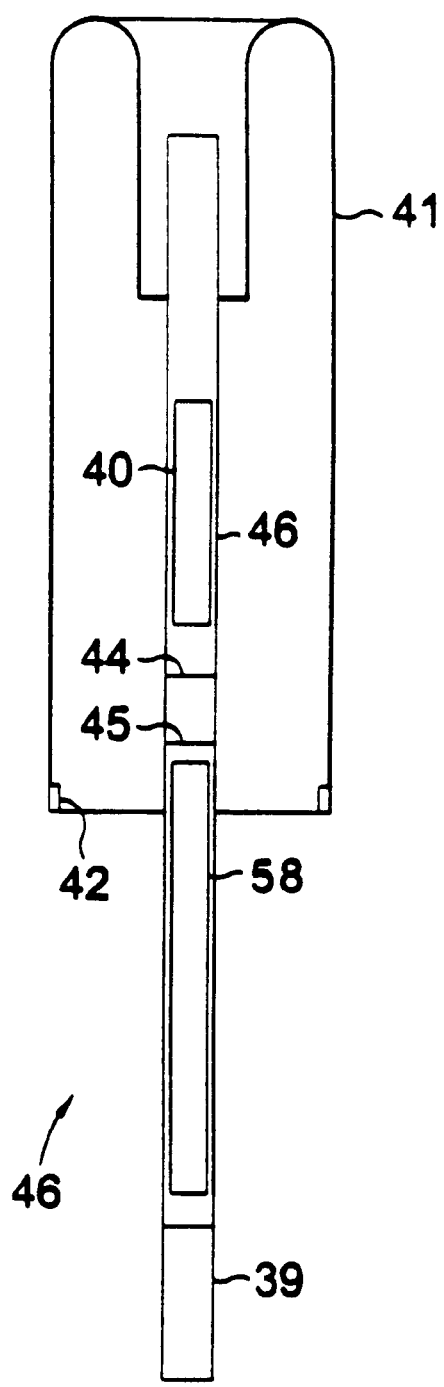
FIG. 19 is a side view of the result stick of an alternate embodiment of the invention.
Figure 20:
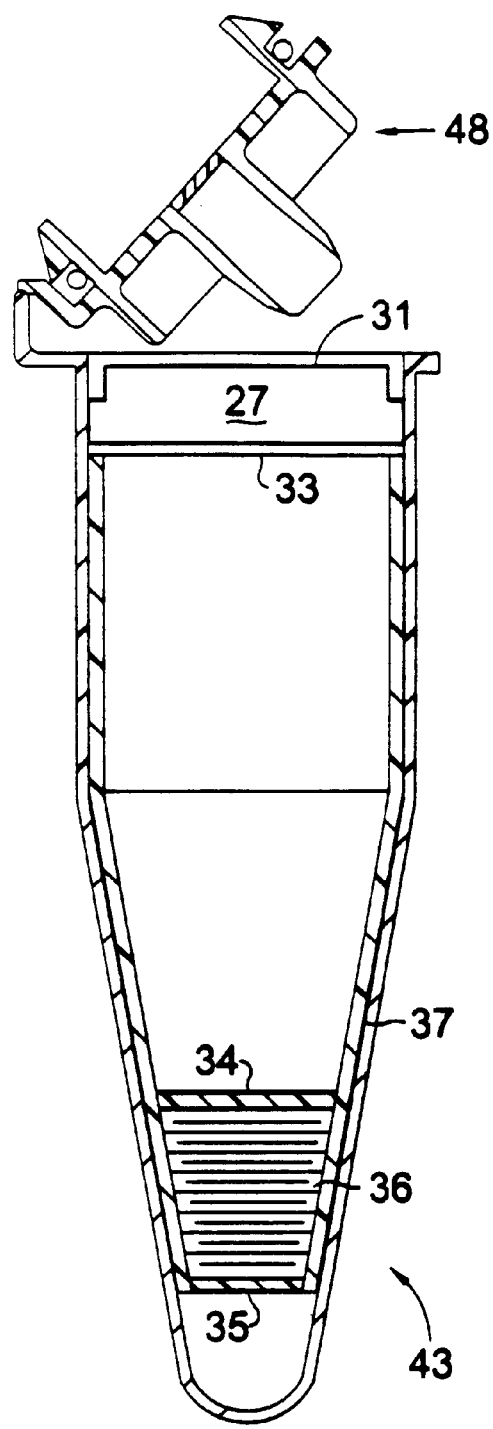
FIG. 20 is side cross-sectional view of the alternate embodiment of the instant invention with the matrix tube inserted inside of the PCR tube with the cap in the opened position.
Figure 21:
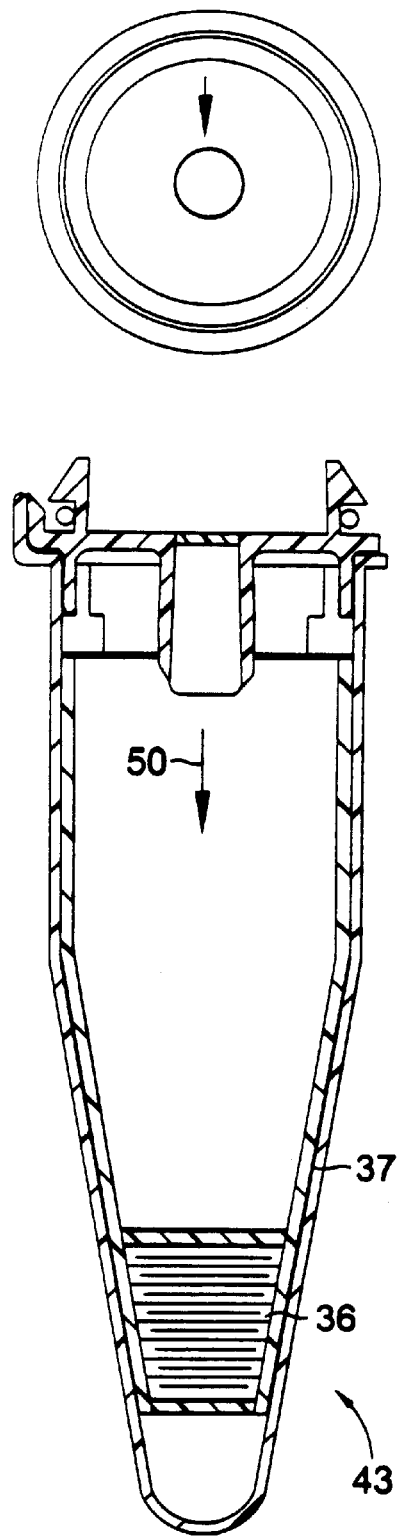
FIG. 21 is a side cross-sectional view of the alternate embodiment of the instant invention with the matrix tube inserted within the PCR tube and the cap in the closed position, and a top plan view of the lid of the alternate embodiment of the invention.

Yet another embodiment of a self-contained device of the invention is illustrated in FIG. 20 and includes a self-contained integrated particle assay device for use with polymerase chain reaction (PCR). This embodiment is defined by a matrix tube 37 (FIG. 17), a PCR tube 43 (FIG. 18), a reagent or reagents 29 which may be contained in a reagent cell 27 (FIG. 16), and a result stick 46 (FIG. 19). The reagent cell 27 (FIG. 16) is further defined by two pouches or chambers: a first pouch 30 containing liquid 28 such as water or other appropriate diluent, and a second pouch containing lyophilized PCR reagents 29. Alternatively, the second pouch may contain a lyophilized reagent bead or beads. Three foil seals, an upper 31, middle 32 and a lower 33 (FIG. 16), are disposed and positioned within the reagent cell 27 such that they separate and contain the liquid 28 and the PCR reagents 29.

PCR reagents 29 include, for example, specific primers for target nucleic acid and control nucleic acid, enzymes, stabilizers, and buffers useful for PCR amplification of target and control molecules. At least two of the target specific primers are labeled with distinct haptens A and B, and at least two of the primers for the control nucleic acid sequence are labeled with distinct haptens C and D. These haptens are incorporated into the target and control amplification products—bifunctional haptenization—during the amplification reaction.

Figure 17:
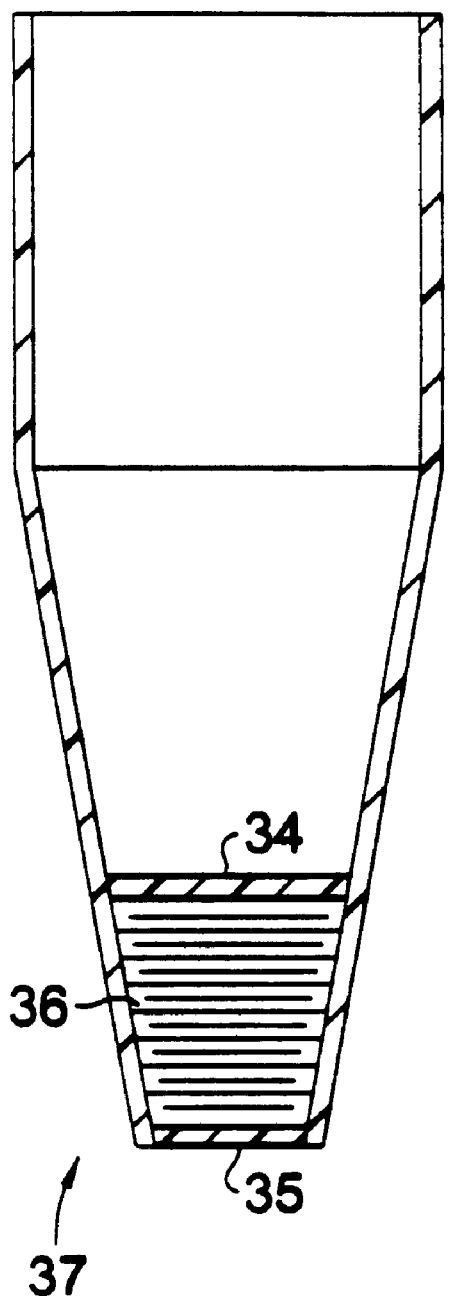
FIG. 17 is a side cross-sectional view of the matrix tube of an alternate embodiment of the invention having a solid phase matrix sandwiched between an upper and lower screen.

In one embodiment of the self-contained device of FIG. 20, matrix tube 37 (FIG. 17) comprises an upper screen 34 and lower screen 35 between which a solid phase matrix 36 specific for nucleic acid binding is sandwiched. In an alternate embodiment (not shown) of the self-contained device of FIG. 20, the solid phase matrix 36 is directly adhered or bound directly to the interior wall of the matrix tube. Thus, it is not a necessary or defining facet of the instant invention that the solid phase matrix 36 be sandwiched between an upper screen 34 and a lower screen 35 as shown in FIG. 17. The solid phase matrix 36 comprises, for example, aluminum oxide or silicon dioxide. The top of the matrix tube 37 may snap fit with a mating and locking connection mechanism, such as a Luer-lock type. The matrix tube 37 is constructed from any material suitable for facilitating thermo-regulation and fluid transfer, such as thin wall or porous plastic. The general shape of matrix tube 37 is that of what is generally known as either a PCR or Eppendorf tube, i.e., a conical-shaped tube having a closing top portion and configured in size such that it is able to be contiguously disposed within the PCR tube 43 of the instant device.

Figure 18:
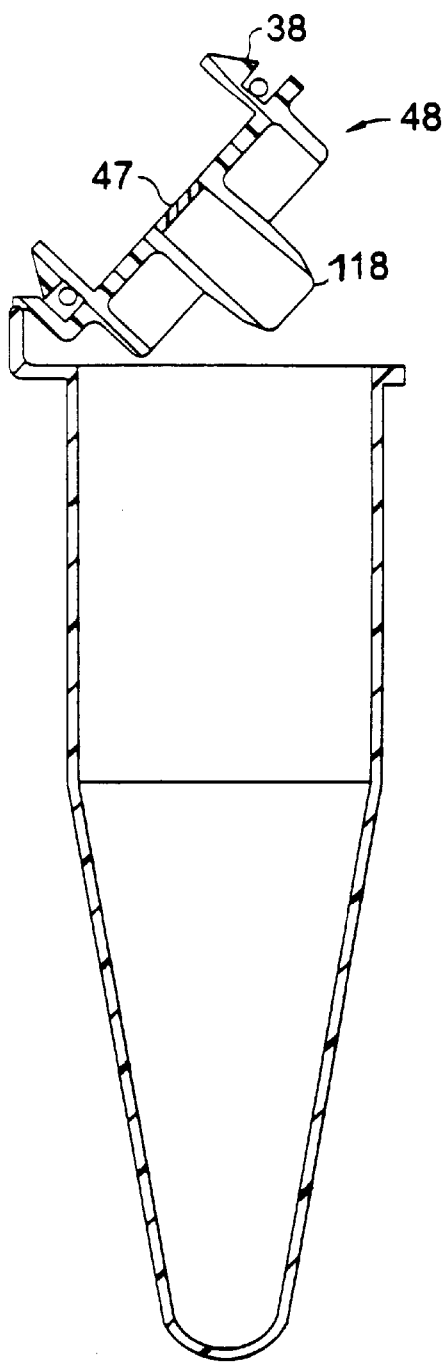
FIG. 18 depicts a side cross-sectional view of the PCR tube of an alternate embodiment of the invention, said tube having a specially designed lid.

Moving now to FIG. 18, the PCR tube 43 is a tube generally accepted in the art as a PCR tube and further contains a foil, plastic, rubber or other elastomer patch 47 disposed on the interior of its lid 48. This patch 47 seals the area through which the result stick 46 (FIG. 19) passes upon its introduction therethrough, after the PCR reaction is complete. The lid 48 may contain a sharp knife-like piercing feature 118 able to pierce all three of the foil seals 31, 32, and 33 of the reagent cell 27 (FIGS. 16 and 20), thus resuspending the reagents 29 in the liquid 28. The PCR tube 43 further contains a locking and/or sealing means 38 within lid 48 that, in turn, seals the entry aperture created upon introduction of the result stick 46 into to the PCR tube 43. For example, the locking or sealing means may include foil, plastic, rubber or other elastomer.

Referring now to FIG. 19, the result stick 46 consists of an elongated transparent body 41, for example plastic or polycarbonate, having a top portion intended for handling the result stick 46 and a bottom portion intended for detection. A snap fit type seal 42 locks the result stick 46 into the PCR tube 43. Moving from the bottom to top portion of the result stick 46, there is disposed thereon an absorbent sample pad 39, a solid phase matrix 58, for example a porous membrane, and a waste pad 40, respectively. The absorbent sample pad 39 is comprised of any generally accepted material suitable for lateral flow and dip stick type assays. The pad 39 is fabricated to contain microparticles conjugated with a receptor specific for hapten A, as well as microparticles conjugated with a receptor specific for hapten C. Alternatively, the microparticles may be on the porous membrane 58 itself. The porous membrane 58 further carries a control indicator line 44 and a sample detection indicator line 45 that have been strategically applied and dried thereon. The sample detection indicator line 45 consists of a receptor specific for hapten B. The control detection indicator line 44 consists of a receptor specific for hapten D.

The operating sequence of the embodiment of the self-contained device illustrated in FIGS. 16–22 entails adding a sample containing the target nucleic acid (if present) and a control nucleic acid in lysis buffer to the matrix tube 37 directly or through a suitable vessel. A suitable vessel may include, for example, a syringe that snap fits onto the matrix tube 37 via a mating and locking connection system. After denaturization, the sample passes through the matrix tube 37 into a waste area, and the target and control nucleic acids bind specifically to the solid phase matrix 36. The sample passes through the tube via, for example, gravity flow or any suitably adaptable method, such as vacuum controlled flow. Next, the matrix-bound nucleic acids are washed with suitable buffer and the matrix tube 37 is placed into the PCR tube 43 (FIG. 20). The reagent cell 27 is inserted into the PCR tube 43 as illustrated in FIG. 20. By pushing firmly on the cap 48 of the PCR tube 43 the foil seals 31, 32 (not shown) and 33 of reaction cell 27 are pierced, thus causing reagent 29 (not shown) to be resuspended in liquid 28 (not shown). The liquid resuspension drops to the bottom of the matrix tube 37 and PCR tube 43 as shown by arrow 50 in FIG. 21 and enters the solid phase matrix 36. Reaction volume is calculated to be sufficient such that the solid phase matrix 36 lies below the meniscus created by the reaction reagents. The PCR tube 43 (FIG. 21) containing the matrix tube 37, resuspended reagents 29 and nucleic acid bound to the solid phase matrix 36 is then inserted into a thermocycler for amplification of the target and control sequences. In one embodiment, the amplification produces bifunctionally labeled target nucleic acids labeled with haptens A and B, and bifunctionally labeled control nucleic acids labeled with haptens C and D.

Figure 22:
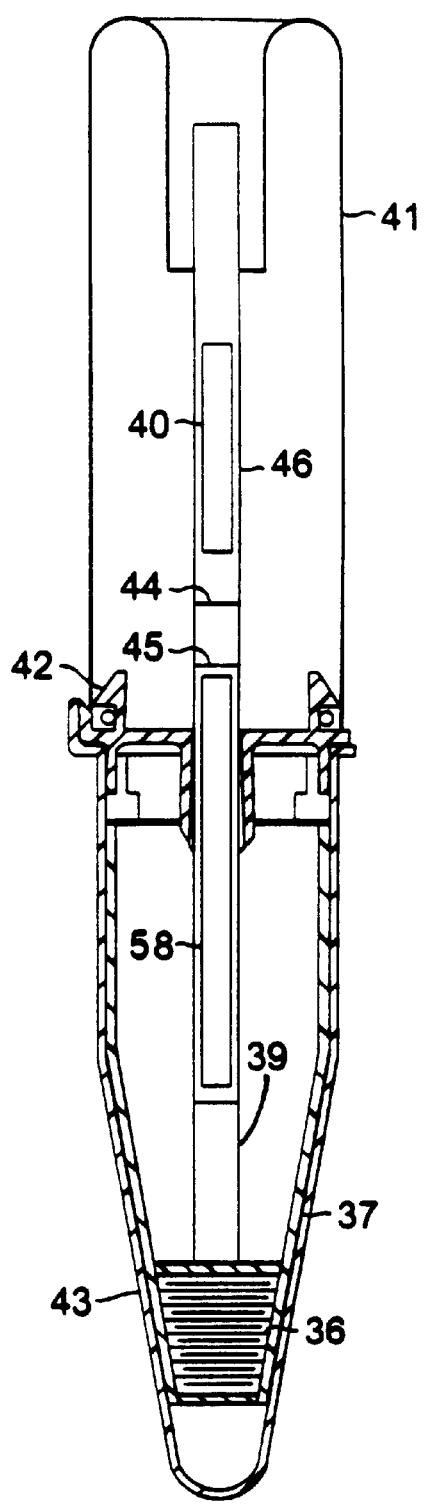
FIG. 22 is a side cross-sectional view of the alternate embodiment of the invention, showing detection via a result stick.

Upon completion of the PCR event, the device is removed from the thermocycler and the result stick 46 is inserted into the PCR tube 43 through the foil patch 47 in the lid 48 (FIG. 22). The absorbent sample pad 39 of the result stick 46 comes into contact with the aqueous reaction mixture containing amplified target nucleic acid (if target was present in the sample) and amplified control nucleic acid. The mixture soaks into or wicks up the absorbent sample pad 39 where the microparticles coated with either receptors A' or C' bind to their respective haptens. That is, microparticles coated with receptors A' bind to haptens A on target nucleic acids, and microparticles coated with receptors C' bind to haptens C on control nucleic acids. Once the absorbent pad 39 is saturated, the reaction mixture and the nucleic acid-bound microparticles wick up the porous membrane 58 via capillary flow toward the control and sample detection indicator lines 44 and 45, respectively. Wicking is facilitated by the presence of the waste pad 40. If the target nucleic acid is present, hapten B on the microparticle-bound target nucleic acid binds to a receptor B' contained in the target detection indicator line 45, forming a visible line of detection. Also, haptens D on the microparticle-bound control sequences bind to receptors D' contained in the control detection indicator line 44, forming a visible line. The detection results are viewed through the transparent body 41 of the result stick 46.

3. Microparticle Selection

The preferred microparticles utilized in this invention are composed of polymeric materials such as latex, polyethylene, polypropylene, poly(methyl methacrylate) or polystyrene. The preferred microparticle in the present invention is composed of latex containing a colored dye. However, a variety of other synthetic or natural materials may also be used in the preparation of the microparticles, for example, silicates, paramagnetic particles and colloidal gold. The usual form of microparticles possesses surface sulfate charge groups that can be modified by the introduction of functional groups such as hydroxyl, carboxyl, amine and carboxylate groups. The functional groups are used to bind a wide variety of ligands and receptors to the microparticles. These groups are selected on the basis of their ability to facilitate binding with the selected member of the ligand-receptor pair. Conjugation of the receptors to the microparticle is accomplished by covalent binding or, in appropriate cases, by adsorption of the receptor onto the surface of the microparticle. Techniques for the adsorption or covalent binding of receptors to microparticles are well know in the art and require no further explanation. The preferred method of attachment of the receptor to the microparticles is covalent binding.

In the present invention, microparticle-bound receptors are specific for discrete haptens located on the ends of amplified, labeled nucleic acid sequences. The receptors must be capable of binding to their specific binding partner (hapten).

The size of the microparticles used in this invention is selected to optimize the binding and detection of the labeled amplified nucleic acids (amplicons). Microparticles are available in a size range of 0.01 to 10.0 µm in diameter and preferably 0.01 to 1.0 µm in diameter, specifically not excluding the use of either larger or smaller microparticles as appropriately determined. The microparticles are activated with a suitable receptor for binding to the target ligand.

In one embodiment, the microparticles are anti-digoxigenin Fab-coated microparticles. To prepare the anti-digoxigenin-coated microparticles, 0.25 to 1.0 mg/mL of anti-digoxigenin Fab is incubated with a suspension containing a final concentration of 1.0% microparticles/mL. The microparticles and digoxigenin Fab are allowed to react for 15 minutes prior to treatment with an activating agent such as EDAC (1-ethyl-3-(3-dimethylaminopropyl) carbodiimide) for covalent binding. The microparticles are treated with EDAC at a final concentration of 0.0 to 2.5 mM. The Fab and microparticles are mixed and incubated at room temperature for one hour. Unbound Fab is removed by successive washes and the coated microparticles are resuspended in storage buffer.

4. Amplification

The present invention employs a variety of different enzymes, such as polymerases and ligases, to accomplish amplification of target nucleic acid sequences. Polymerases are defined by their function of incorporating nucleoside triphosphates to extend a 3' hydroxyl terminus of a "primer molecule." As used herein, a "primer" is an oligonucleotide that, when hybridized to a target nucleic acid molecule, possesses a 3' hydroxyl terminus that can be extended by a polymerase and a hapten label at or near the 5' terminus. For a general discussion concerning polymerases, see Watson, J. D., et al., *Molecular Biology of the Gene*, 4th Ed., (1987) W. A. Benjamin, Inc., Menlo Park, Calif. Examples of polymerases that can be used in accordance with the methods described herein include, but are not limited to, *E. coli* DNA polymerase I, which is the large proteolytic fragment of *E. coli* polymerase I and is commonly known as "Klenow" polymerase, Taq-polymerase, T7 polymerase, T4 polymerase, T5 polymerase and reverse transcriptase. The general principles and conditions for amplification of nucleic acids using polymerase chain reaction are well known in the art.

The preferred amplification methodologies for use in the self-contained devices of this invention include isothermal reactions such as nucleic acid sequence-based assay (NASBA) disclosed in U.S. Pat. No. 5,130,238, which is specifically incorporated herein, and strand displacement assay (SDA) disclosed by Walker, et al., *PNAS* 89:392 (1992), which is specifically incorporated herein by reference. Another amplification methodology for use in this invention includes polymerase chain reaction (PCR).

With amplification, certain specimens are inhibitory to the amplification reaction, providing false-negative results. To avoid this problem, a positive control—a control nucleic acid with primer recognition sequences attached to a totally irrelevant nucleic acid sequence—is incorporated in the amplification step. This positive control primer is a component of the nucleic acid extraction reagents, thus controlling for sample extraction and delivery as well as detecting amplification failure. The preferred embodiment of the positive control is a lambda DNA sequence. The control nucleic acid is extracted and amplified along with the target nucleic acid and is detected by a line of immobile, coated microparticles on the detection membrane.

The target oligonucleotide primer and the control oligonucleotide primer used in the amplification steps of this invention contain at least one hapten as a label which does not participate in the priming reaction. The hapten is bound to at least one position of the nucleic acid primer. For the derivatization of nucleic acid primers, various methods can be employed. See, Sambrook supra. The incorporation of the hapten can take place enzymatically, chemically or photochemically. The hapten can be derivatized directly to the 5' end of the primer or contain a bridge 1 to 30 atoms long. In the preferred embodiment, the bridge is linear. However, in an alternate embodiment, the bridge consists of a branched chain with a hapten molecule on at least one of the chain ends. By means of the presence of several hapten molecules on the ends of a branched chain, the detection sensitivity is increased. The preferred haptens for the present invention are biotin and digoxigenin, however, other haptens having a receptor as specific binding agent available are suitable, for example, steroids, halogens and 2,4-dinitrophenyl.

The self-contained devices disclosed herein provide for extremely rapid, economical nucleic acid detection. Further, the self-contained devices significantly reduces the risk of cross contamination in that neither amplification reagents nor amplicons are manipulated. Elimination of cross contamination opens the door to mass screening including automation.

The self-contained devices of the present invention can be used in the diagnoses of infectious diseases of genetic, bacterial or viral origin. The high sensitivity of analysis using the self-contained devices of this invention allows for the early detection of disease and an opportunity for early treatment. Analysis by this invention may monitor the efficacy of treatment, for example, to monitor HIV virus in the plasma of patients undergoing therapy. The low complexity of the device lends itself to "point of care" testing in clinics and physician's offices. The portability of the device provides for "on site" analysis to detect nucleic acid sequences in the areas of forensics, agriculture, environment and the food industry.

The cost of nucleic acid analysis using the self-contained devices of this invention is significantly less than other methods currently in use to detect amplified nucleic acids. The time frame for detecting an amplified sequence is reduced drastically. There is no danger from potentially hazardous chemicals. The analysis does not require special waste disposal procedures. The requirements of many washes in an immunometric or hybridization approach are eliminated. The self-contained device does not require special equipment, other than a standard, constant temperature heat block.

The following examples serve to explain and illustrate the present invention. The examples are not to be construed as limiting of the invention in anyway. Various modifications are possible within the scope of the invention.

EXAMPLE 1

Isothermal Amplification Approach to Detection with Labeled Amplified Target Sequence Using NASBA One preferred amplification methodology for use in this invention is an isothermal reaction such as nucleic acid sequence-based assay (NASBA). The primary product of the NASBA reaction is single strand RNA. The NASBA reaction utilizes a primer containing a T7 polymerase promoter. Following T7 transcription, up to 100 copies of target RNA are produced. These copies are the same sequence as the original target RNA. They serve as templates, thus starting the cycle again and resulting in up to a billion fold amplification of the original template.

In order to incorporate NASBA into the devices disclosed herein, probes that allow the formation of a bifunctionally haptenized amplification product have been designed. For NASBA there are two possible strategies: 1) design amplification primers that are haptenized; and 2) use two haptenized capture oligonucleotides which bind to the product RNA. The model system chosen is to the HIV POL gene.

Figure 14:
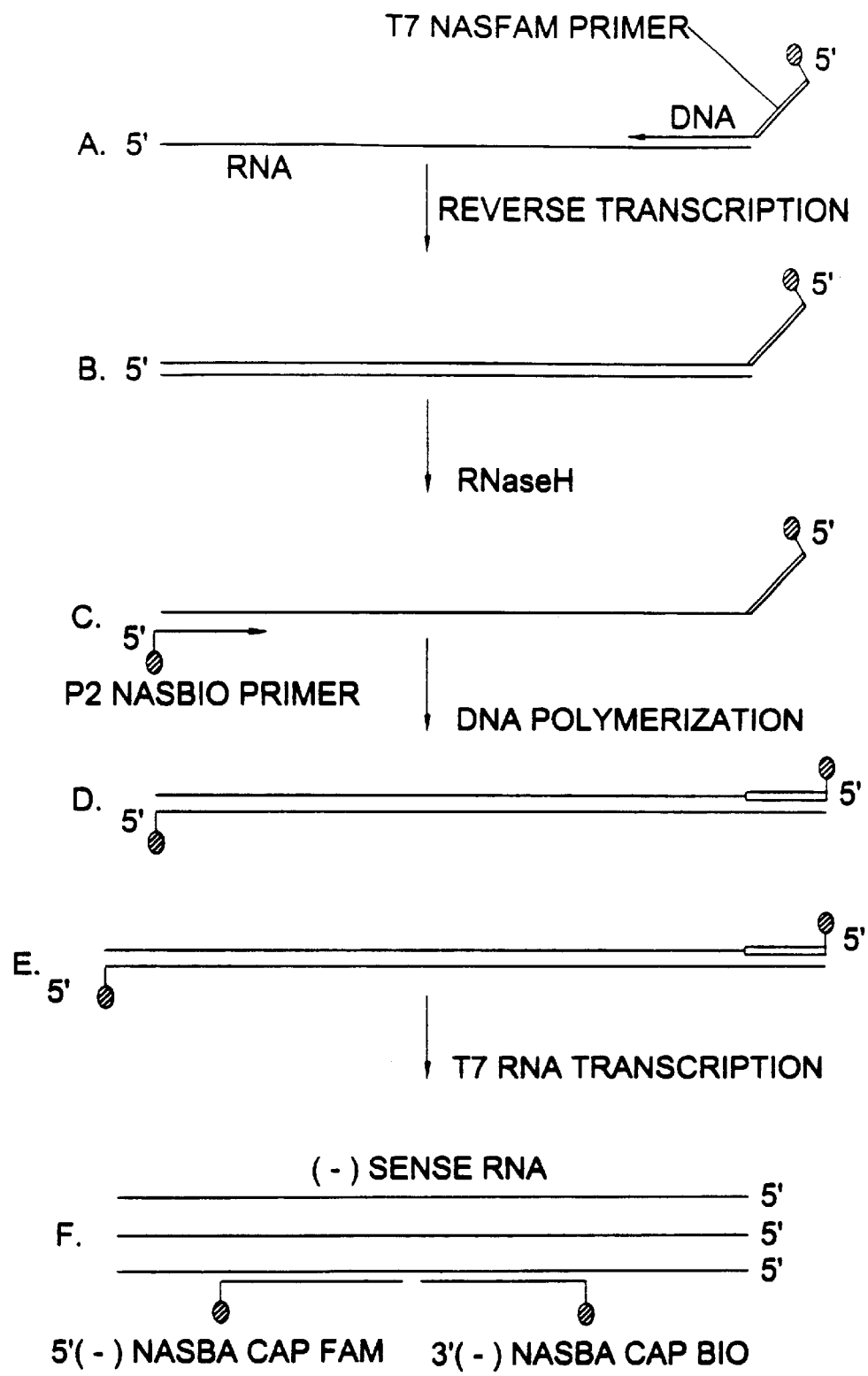
FIG. 14 depicts a nucleic acid sequenced-based amplification (NASBA) strategy.

The first strategy using NASBA haptenization, i.e., the design of amplification primers that are haptenized, is illustrated in FIG. 14, steps A–D. A T7 NASFAM haptenization primer, containing a T7 transcriptase promoter and an attached fluorescein, binds to the target RNA (FIG. 14, step A). A reverse transcriptase transcribes a DNA copy of the RNA, as illustrated in step B of FIG. 14. The original RNA strand is digested by RNase H. A reverse haptenization primer, P2 NASBIO with attached biotin, binds to the antisense DNA (FIG. 14, step C) and is extended by the DNA polymerase activity of the reverse transcriptase. The haptenized primers are as follows:

T7 NASFAM (T7-promoter primer):

5'-fluorescein-AATTCTAATACGACTCACTATAGGGTGC-
      TATGTCACTTCCCCTTGGTTCTCT-3'      SEQ ID NO: 1

P2 NASBIO (reverse primer):

5'-biotin-AGTGGGGGGACATCAAGCAGCCATG
      CAAA-3'      SEQ ID NO: 2

The resulting double-stranded bi-haptenized DNA intermediate, containing a biotin label at one end and a fluorescein label at the other end, is illustrated in step D of FIG. 14. This complex gives signal in lateral flow or slide agglutination assays.

The second strategy for using NASBA in this invention, i.e., the use of two haptenized oligonucleotides which bind to the product RNA, is illustrated in FIG. 14, steps E–F. T7 RNA polymerase binds to the promoter region (step E) to manufacture many copies of a minus-sense RNA, as shown in steps E and F of FIG. 14. This RNA contributes to the manufacture of the DNA intermediate by similar means. Two capture oligonucleotides, each having one hapten of either fluorescein or biotin, bind to the minus-sense RNAs (FIG. 14, step F) giving bifunctional haptenized complexes. These complexes give signal in lateral flow or slide agglutination. The haptenized capture oligonucleotides, designed to bind to the minus-sense RNA product are:

5'(-)NASBA CAP FAM:

5'-fluorescein-TGGCCTGGTGCAATAGGCCC-3'    SEQ ID NO: 3

3'(-)NASBA CAP-BIO:

5'-CCCATTCTGCAGCTTCCTCA-biotin-3'    SEQ ID NO: 4

EXAMPLE 2

Isothermal Amplification Approach to Detection with Bifunctionally Labeled Amplified Target Sequence Using Strand Displacement Assay The instant strand displacement assay (SDA) is another example of an isothermal amplification methodology that can be detected in the self-contained devices of this invention by using microparticles and bifunctionally labeled product.

SDA technology is described in U.S. Pat. No. 5,455,166 which is specifically incorporated herein. SDA is isothermal amplification based on the ability of a restriction enzyme to nick the unmodified strand of a hemiphosphorothioate from its recognition site and the ability of DNA polymerase to initiate replication at the nick and displace the downstream non-template strand. Primers containing recognition sites for the nicking restriction enzyme bind to opposite strands of target DNA at positions flanking the sequence to be amplified. The target fragment is exponentially amplified by coupling sense and antisense reactions in which strands displaced from the sense reaction serve as a target for the antisense reaction and vice versa.

Figure 8:
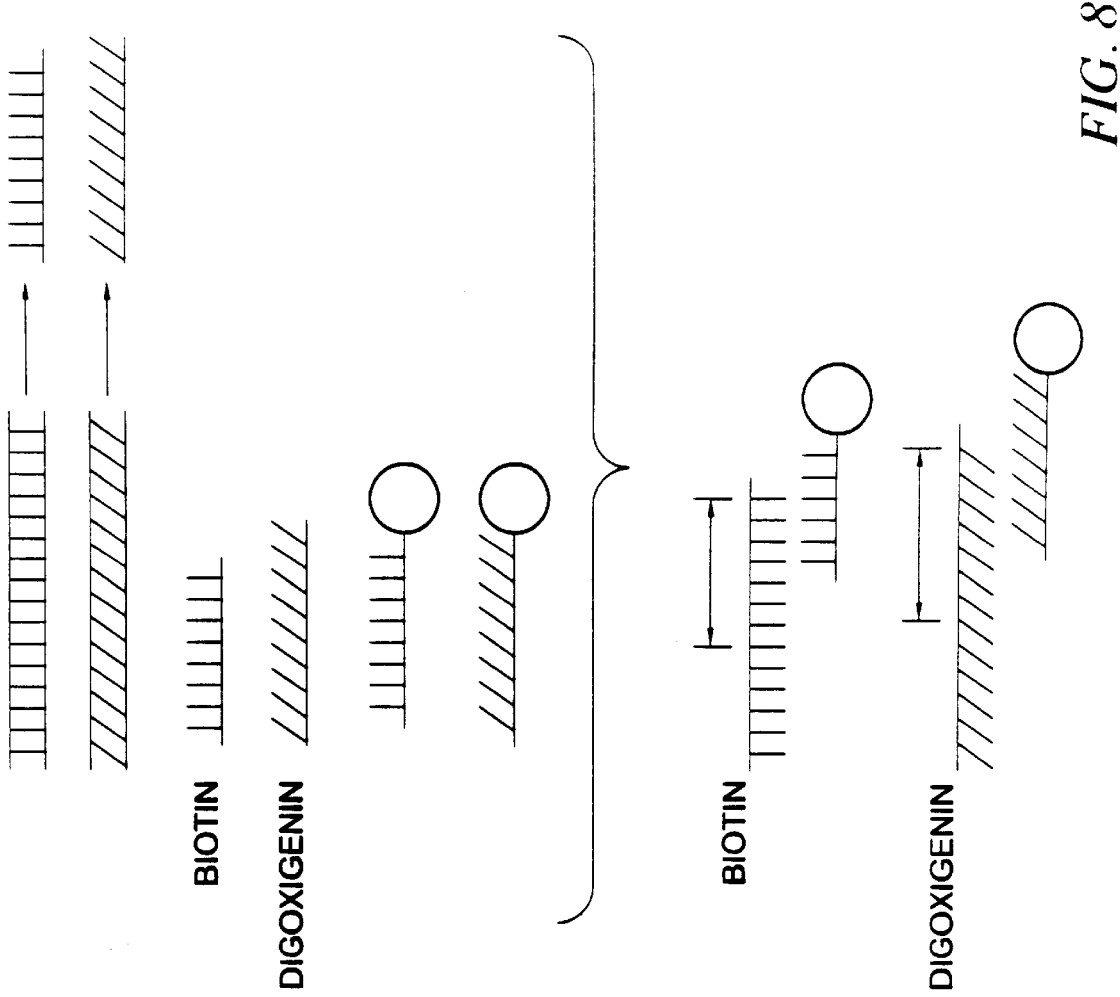
FIG. 8 illustrates the reagents and their respective interactions in the amplification chamber of the device in a strand displacement assay (SDA) strategy.
Figure 9:
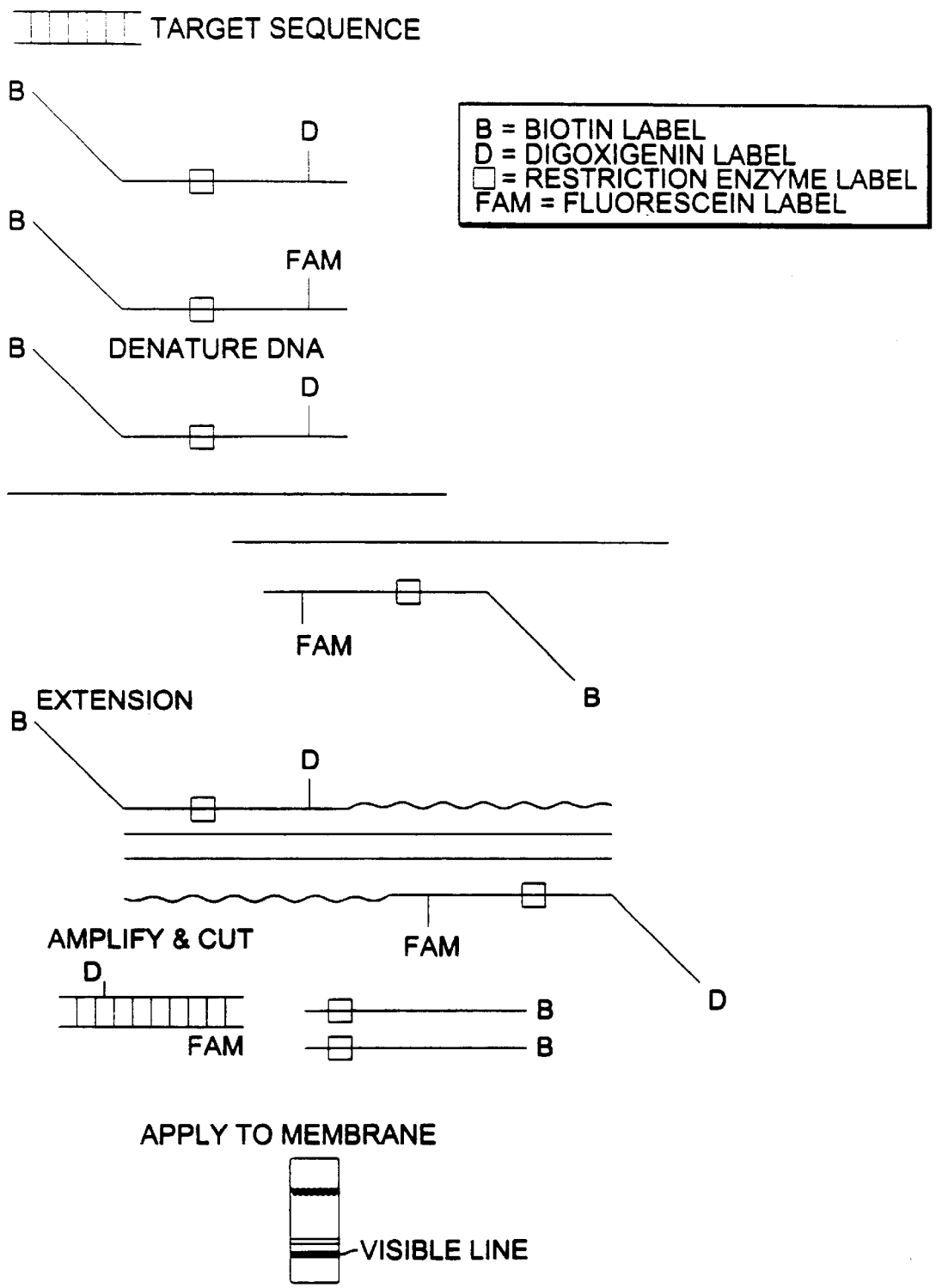
FIG. 9 depicts reagents and their respective interactions in an alternate strand displacement assay (SDA).

This set of experiments is conducted with composite extension primers that are labeled with biotin, fam or digoxigenin (FIGS. 8 and 9). Bumper primers are the same sequence as provided by Becton Dickinson and Company (Franklin Lakes, N.J.). The sequences of the target, the bumper primer and the composite extension primer are as follows:

Bumper primers:

B1: 5'-CGATCGAGCAAGCCA    SEQ ID NO: 5

B2: 5'-CGAGCCGCTCGCTGA    SEQ ID NO: 6

Composite extension primers:

S1: 5'-fam/dig-ACCGCATCGAATGCATGTCTCGGGTAAG-
        GCGTACTCGACC    SEQ ID NO: 7

S2: 5'-biotin-CGATTCCGCTCCAGACTTCTCGGGTG-
        TACTGAGATCCCCT    SEQ ID NO: 8

Target sequence:

5'-TGGACCCGCCAACAAGAAGGCGTACTC-
    GACCTGAAAGACGTTATCCACCAT ACGGATAGGG-
    GATCTCAGTACACATCGATCCGGTTCAGCGSEQ ID NO: 9

The reaction is set up per the thermophilic Strand Displacement Amplification (tSDA) protocol developed by Becton Dickinson and Co. The target organism is *Mycobacterium tuberculosis*. For pilot studies, an artificial target template consisting of the 91 nt sequence of the *M. tuberculosis* genome, defined by the Becton Dickinson outer (bumper) primers, is used. Amplification conditions used are identical to those used by Becton Dickinson for tSDA.

The membrane used for this procedure is nitrocellulose, purchased from Millipore Corporation, Bedford, Mass. A stripe of streptavidin at a concentration of 1 mg/mL is applied at a rate of 1 μL/cm via a linear reagent striper (IVEK Corporation, No. Springfield, Vt.) 1 cm from the bottom edge of the membrane. After application of the streptavidin, the membrane is allowed to dry and then blocked for non-specific binding by 0.5% casein in 100 mM Tris, pH 7.4. The membrane is washed twice with water (ddH₂O) and allowed to dry.

Next, 3 μL of anti-S1 extension primer (complementary to S1 without the biotin label) and/or S2 extension primer (complementary to S2 without the dig or fam label) is spotted onto a second membrane. The second membrane is then sandwiched onto the first membrane in order to capture free primers that compete with the product for the microparticles or streptavidin capture zone.

The coated microparticles are prepared as described above by incubating either anti-digoxigenin Fab or anti-fam monoclonal IgG with a suspension of microparticles. The coated microparticles are diluted 1:2 with a 35% sucrose solution, and 3 μL or the solution is applied directly to the membrane and dried.

Figure 11:
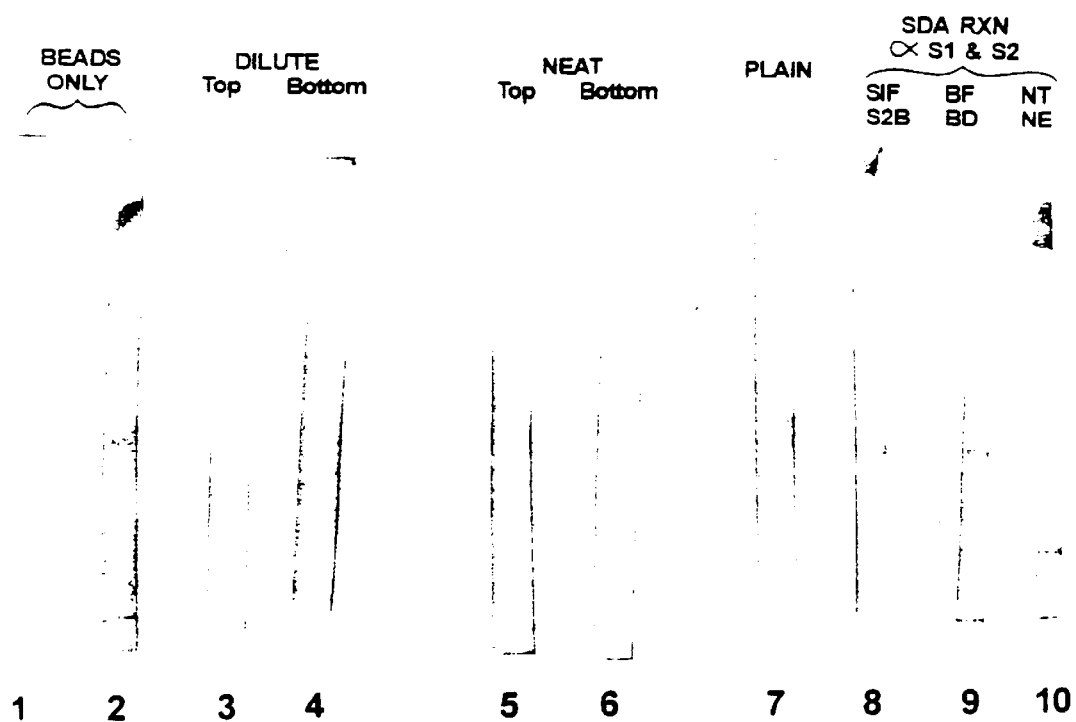
FIG. 11 illustrates the detection results of isothermal amplification and detection with bifunctionally labeled amplified target sequence using strand displacement assay.

The bifunctionally labeled reaction product (10 μL) is added to 45 μl SDA buffer, then applied (50 μL) to the previously striped membrane. Application of the sample requires the bifunctionally labeled product and the competing primers to pass through the anti-primer coated membrane and the dried microparticles. When the target is present, there is a visible line on the membrane. When the target is not present, there is absence of a visible line. The results of one such experiment are shown in FIG. 11.

EXAMPLE 3

Inhibition Assay: Loss of Visible Signal on Lateral Flow Membrane

Figure 10:
FIG. 10 depicts the reagents and their respective interactions in a cycling probe assay.

Cycling probe technology involves a nucleic acid probe that incorporates DNA-RNA-DNA sequences designed to hybridize with the target sequences. See, for example, FIG. 10. The probe is bifunctionally labeled with biotin and fam. If the probe hybridizes with the target generating double stranded nucleic acid, RNase H in the reaction buffer cleaves the probe. This cleavage results in loss of signal when applied to a membrane containing a capture zone of streptavidin and anti-fam coated colored microparticles. If the target is not present, there is a visible line on the membrane.

The specific probe and target employed in the instant example have been designed by ID Biomedical Corporation for use in detecting *Mycobacterium tuberculosis*. The probe (SEQ ID NO: 10) is a chimeric construct containing both DNA and RNA sequences with labels on the 5' (fam) and the 3' (biotin) ends of the DNA portion of the probe. The binding of the probe to a single strand of target generates double stranded nucleic acid which is cleaved with RNase H, thus eliminating the bifunctionality of the probe. The sequence of the probe is described below:

FARK2S3B probe

5'-fam-AAAGATGTagagGGTACAGA-biotin-3'    SEQ ID NO: 10

(lower case indicates ribonucleoside bases)

The sequence of the target is described below:

ARK2-T synthetic target

5'-AATCTGTACCCTCTACATCTTTAA-3'    SEQ ID NO: 11

The reaction is completed following the protocol provided by ID Biomedical Corporation. The membrane used for this procedure is nitrocellulose, purchased from Millipore Corporation, Bedford, Mass. A stripe of streptavidin at a concentration of 1 mg/mL is applied at a rate of 1 μL/cm via a linear reagent striper (IVEK Corporation, No. Springfield, Vt.) 1 cm from the bottom edge of the membrane. After application of the streptavidin, the membrane is allowed to dry and then blocked for non-specific binding by 0.5% casein in 100 mM Tris, pH 7.4. The membrane is washed twice with water (ddH₂O) and allowed to dry. The microparticles used are anti-fam coated microparticles prepared as described above using anti-fam monoclonal IgG.

Figure 12:
FIG. 12 shows the detection results of a lateral flow assay using cycling probe technology.

The reaction product (10 μL) is added to 5 μl of 0.1% anti-fam coated microparticles (0.1%) and 35 μL of water, then applied (50 μL) to the previously striped membrane. The binding of the bifunctionally labeled probe to the target, followed by cleavage of the probe by RNase H, results in loss of the bifunctionality of the probe. When the target is present, the absence of a visible line on the membrane exists. When the target is not present, the bifunctionally labeled probe is able to bind the anti-fam coated microparticles and the streptavidin bound to the membrane, resulting in a visible line. The results of one such experiment are shown in FIG. 12.

EXAMPLE 4

Detection of Bifunctionally Labeled Amplified Product

The membrane used for this procedure is nitrocellulose, purchased from Millipore Corporation, Bedford, Mass. A stripe of streptavidin at a concentration of 1 mg/ml is applied at a rate of 1 μL/cm via a linear reagent striper (IVEK Corporation, No. Springfield, Vt.) 1 cm from the bottom edge of the membrane. After application of the streptavidin, the membrane is allowed to dry and then blocked for non-specific binding by 0.5% casein in 100 mM Tris, pH 7.4. The membrane is washed twice with water (ddH$_2$O) and allowed to dry.

Figure 13:
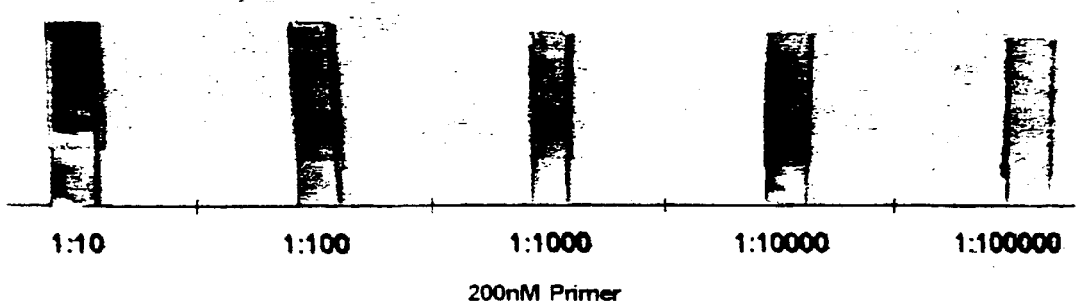
FIG. 13 shows the detection results of an alternate lateral flow assay.
Figure 13:
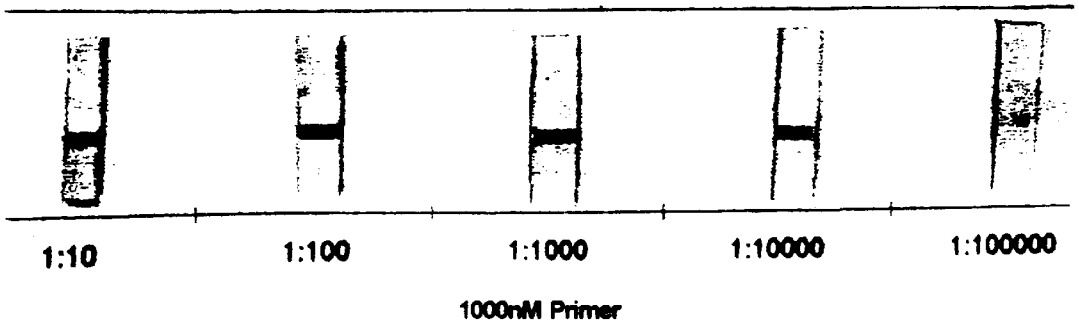

The amplification product is added to the membrane with colored receptor coated beads at dilutions of 0.001–1.0% microparticles/mL. This mixture is allowed to wick up the membrane. Positive reactions result in a colored line where the capture material is applied. Amplification reactions without the target sequence added to the reaction serve as negative controls. The results of this lateral flow assay are illustrated in FIG. 13.

If the target and control nucleic acid sequences are present, the receptor-bound microparticles interact with hapten(s) to capture the amplified nucleic acid. The result is a line of dyed particles visible on the membrane for the target and a line for the control nucleic acids. If the target is not present, the dyed particles for the target are not captured and are not visible. When the result of the analysis is negative, the control nucleic acid sequences must be visible indicating that the extraction and amplification were performed correctly.

EXAMPLE 5

Detection by Amplification with a Single Labeled Primer Followed by Hybridization with a Probe That Contains a Single Label The target nucleic acid sequence is amplified by PCR using 200–1000 mM primer concentration, GeneAmp EZ rTth RNA PCR kit (Perkin Elmer Corp., Alameda, Calif.) and $10^6$ copies/mL of the target HIV RNA sequence. Forty PCR cycles, each cycle being 60° C. for 15 minutes, 95° C. for 15 seconds, and 55° C. for 60 seconds, are run.

The sequences of the primers are as follows:
SK38 Dig Primer:

5'-dig-ATAATCCACCTATCCCAGTAGGAGAA
AT-3'                                            SEQ ID NO: 12

SK39 Primer:

5'-TTTGGTCCTTGTCTTATGTCCAGAATGC-3' SEQ ID NO: 13

Specific PCR reaction conditions are described below:

| Reagent | Final conc. |
| --- | --- |
| 5X EZ Buffer | 1X |
| Mn(OAc)$_2$ | 3 mM |
| rTth polymerase | 5 U |
| dntp's | 240 μM each |
| SK38 | 1 μM |
| SK39 | 1 μM | rTth DNA Polymerase (Perkin Elmer N808-0097)

The SK38 Dig—SK39 amplicon (5 μl) is incubated with 5 μL of 25 μM (125 pmol) SK39 biotin at 95° C. for 1 minute, and then at 55° C. for 1 minute. The amplicon binds to the anti-digoxigenin-coated microparticles and wicks through the membrane to the streptavidin line where it is captured by the interaction of biotin and streptavidin. The result is a visible line of colored microparticles.

Figure 15:
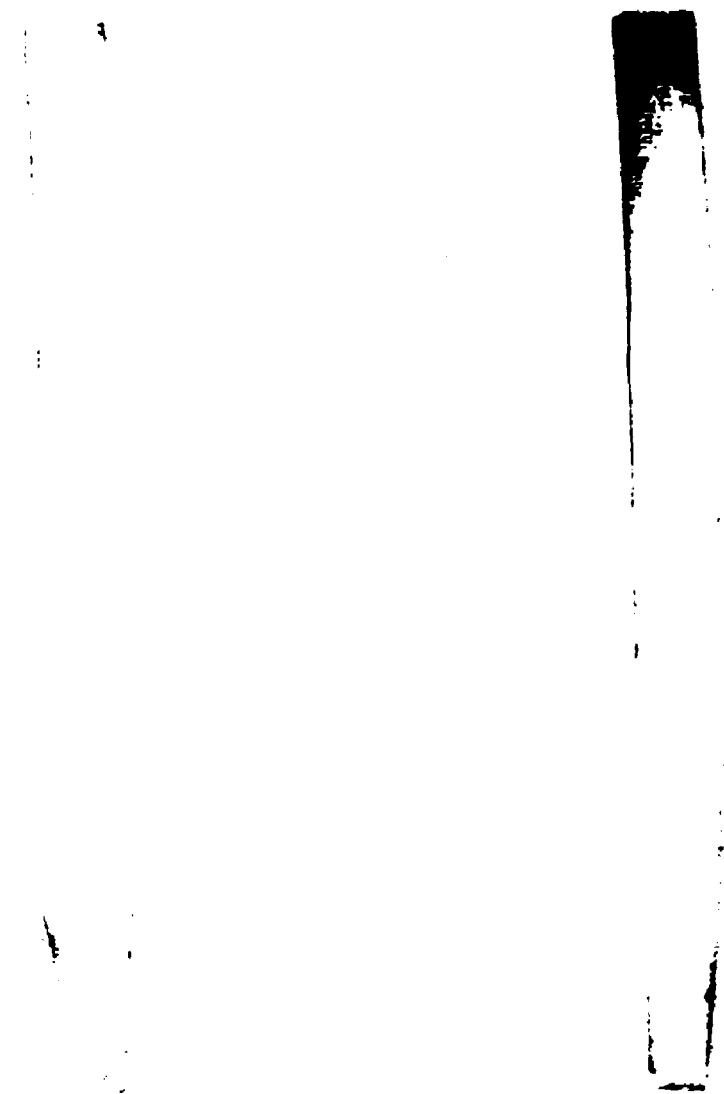
FIG. 15 shows the results of detection by amplification with a single labeled primer followed by hybridization with a probe containing a single label.

In the negative control, the procedure is performed as described above, but without the addition of the target sequence. Without the presence of the target sequence in the amplification reaction, the bifunctionally labeled amplicon is not generated and the visible line of detection is not present. The results of one such experiment are shown in FIG. 15.

EXAMPLE 6

Extraction of Nucleic Acids with Guanidine Thiocyanate onto Glass (Silicon Dioxide) and Subsequent Amplification Without Elution from Silicon Dioxide A column was constructed using Ansys 0.4 mm membrane as a filter to contain the silicon dioxide and a syringe apparatus to pull buffer through the column in approximately 15 seconds. 50 μl serum, 2 μl SiO$_2$ (0.5 mg/ml), and 450 μl guanidine thiocyanate (GuSCN) lysis buffer are mixed by vortexing and then incubated at room temperature for 10 minutes. The specific lysis buffer for the instant set of experiments contains 14.71 g GuSCN (4M final), 0.6 ml TRITON X-100™, 5.5 ml 0.2 M EDTA pH 8.0 and is q.s. to 31.11 mL with 0.1M Tris-HCl to pH 6.4. The silicon dioxide is washed twice with 500 ul 70% EtOH.

Next, the filter with SiO$_2$ is removed from the column and the SiO$_2$ is washed off of the membrane using 20 μL water (ddH$_2$O). 5 μL of the silicon dioxide slurry is added to a PCR reaction using standard protocol for HIV model system, as detailed supra in Example 5.

EXAMPLE 7

Cascade Rolling Circle Amplification

Figure 23:
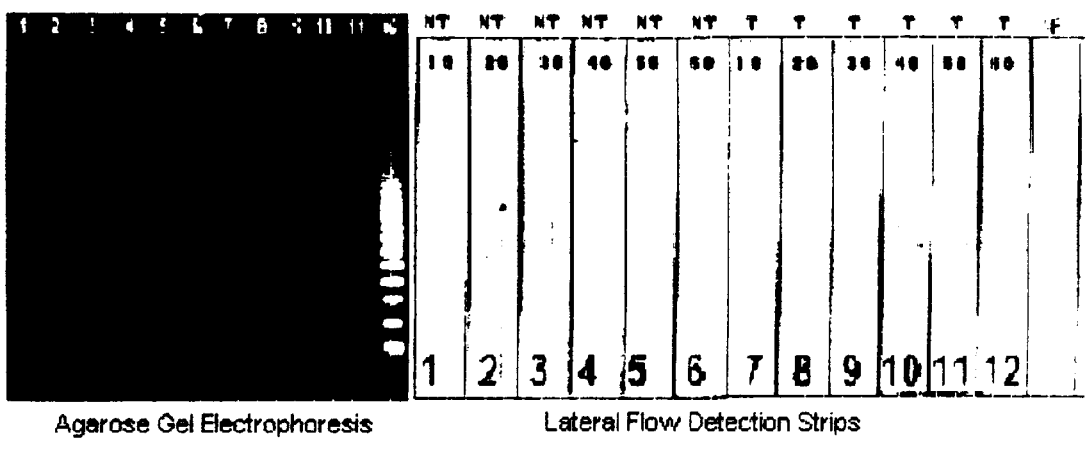
FIG. 23 shows the results of CRCA methodology use for the detection of nucleic acid target sequences in terms of lateral flow detection strips versus gel electrophoresis.

The use of cascade rolling circle amplification (CRCA) and labeled primers for detection of target nucleic acid sequences was established in collaboration with Dr. David Thomas (Oncormed, Inc.). Amplicon from an HIV DNA plasmid model system was bifunctionally labeled during CRCA using tagged primers and subsequently detected by lateral flow chromatography. See FIG. 23. The target sequence was amplified 6 individual times at 10 minute increments. That is, amplification was performed for 10, 20, 30, 40, 50 and 60 minutes, respectively. FIG. 23 shows that the results of agarose gel electrophoresis show no visible results except for the target that was amplified for 60 minutes. Lateral flow chromatography detection strips demonstrate visual detection after 40 minutes of target amplification and a strong visual signal for both the 50 and 60 minute amplifications. These results support the use of an isothermal amplification platform with the self-contained device disclosed herein.

The instant invention provides a rapid, simple and accurate method of detecting amplified target nucleic acid sequences with a self-contained device. Sensitivity and specificity of the assay are based on labeling of the target, by incorporating a label or by subsequent hybridization of a labeled probe during the amplification process. The method does not require costly and sophisticated equipment or specially trained personnel, nor does it pose any health hazard.

While the above description contains many specificities, these should not be construed as limitations on the scope of the invention, but rather an exemplification of the preferred embodiment thereof. Many other variations are possible, such as amplifying several target samples in the same reaction mixture, isothermal amplification, utilizing newly discovered polymerases and ligases, etc. Thus the scope of the invention should be determined by the appended claims and their legal equivalents, rather than by the example given.

We claim:

1. A method of detecting a target nucleic acid in a sample, wherein all of said method steps take place within a multi-chambered self-contained device having at least two chambers, said method comprising:
   a) extracting said target nucleic acid, wherein said extraction includes binding said target nucleic acid to a solid phase or silica slurry;
   b) amplifying said target nucleic acid on said solid phase or silica slurry with a first primer having a first label and a second primer having a second label under conditions that preferentially amplify said target nucleic acid to produce an amplification reaction mixture comprising target amplicons having said first label and said second label, wherein prior to amplification said nucleic acid present in a double-stranded form are rendered single-stranded;
   c) transferring said reaction mixture to a detection chamber of said device; and
   d) detecting said target amplicons within said detection chamber by a lateral flow assay, wherein said assay comprises wicking said target amplicons onto a membrane, wherein said target amplicons bind to at least a first and second reagent and at least one of said reagents is bound to said membrane, whereby when said at least two reagents are both bound to said target amplicons a visible signal is detected, wherein said amplification and said extraction take place within a first chamber of said device that is in fluid communication with said detection chamber, or said extraction takes place within a first chamber of said device and said amplification takes place in a second chamber of said device that is in fluid communication with both said first chamber and said detection chamber.

2. The method of claim 1, wherein said first reagent comprises colored microparticles having first receptors bound thereto, wherein said first receptors bind specifically to said first label on said target amplicons to form microparticle-bound amplicons and said second reagent comprises membrane-bound second receptors that bind specifically to said second label on said amplicons.

3. The method of claim 1, wherein said amplification methodology is polymerase chain reaction (PCR), ligase chain reaction, Qβ replicase, strand displacement assay (SDA), nucleic acid sequence-based amplification (NASBA), or cascade rolling circle amplification (CRCA).

4. A method of detecting a target nucleic acid in a sample, wherein all of said method steps take place within a multi-chambered self-contained device having at least two chambers, said method comprising:
   a) extracting said target nucleic acid, wherein said extraction includes binding said target nucleic acid to a solid phase or silica slurry;
   b) amplifying said target nucleic acid on said solid phase or silica slurry with a first primer having a first label and to a second primer under conditions that preferentially amplify said target nucleic acid to produce an amplification reaction mixture comprising singly labeled target amplicons, wherein prior to amplification said nucleic acid present in a double-stranded form are rendered single-stranded;
   c) transferring said reaction mixture to a detection chamber of said device; and
   d) detecting said target amplicons within said detection chamber by a lateral flow assay, wherein said assay comprises wicking said target amplicons onto a membrane, wherein said singly labeled target amplicons bind to at least a first, a second and a third reagent and at least one of said reagents is bound to said membrane, whereby when said at least three reagents are all bound to said target amplicons a visible signal is detected, wherein said amplification and extraction take place within a first chamber of said device that is in fluid communication with said first chamber, or said extraction takes place within a first chamber of said device and said amplification takes place in a second chamber that is in fluid communication with both said first chamber and said detection chamber.

5. The method of claim 4, wherein said first reagent comprises colored microparticles having first receptors bound thereto, wherein said first receptors bind specifically to said label on said target amplicons, said second reagent comprises a labeled oligonucleotide capable of specifically hybridizing to said target amplicons, and said third reagent comprises receptors bound to said membrane and specific for said label on said oligonucleotide.

6. The method of claim 4, wherein said amplification methodology is polymerase chain reaction (PCR), ligase chain reaction, Qβ replicase, strand displacement assay (SDA), nucleic acid sequence-based amplification (NASBA), or cascade rolling circle amplification (CRCA).

7. A method of detecting a target nucleic acid in a sample, wherein all of said method steps take place within a multi-chambered self-contained device having at least two chambers, said method comprising:
   a) extracting said target nucleic acid, wherein said extraction includes binding said target nucleic acid to a solid phase or silica slurry;
   b) amplifying said target nucleic acid on said solid phase or silica slurry with first and second complementary primers under conditions that preferentially amplify said target nucleic acid to produce an amplification reaction mixture comprising target amplicons, wherein prior to amplification said nucleic acid present in a double-stranded form are rendered single-stranded;
   c) transferring said reaction mixture to a detection chamber of said device; and
   d) detecting said target amplicons within said detection chamber by a lateral flow assay, wherein said assay comprises wicking said target amplicons onto a membrane, wherein said target amplicons bond to at least a first reagent, a second reagent, a third reagent, and a fourth reagent, and at least one of said reagents is bound to said membrane, whereby when said at least four reagents area all bound to said target amplicons a visible signal is detected, wherein said amplification and extraction take place within a first chamber of said device that is in fluid communication with said first chamber, or said extraction takes place within a first chamber of said device and said amplification takes place within a second chamber that is in fluid communication with both said first chamber and said detection chamber.

8. The method of claim 7, wherein said first reagent comprises an oligonucleotide comprising a first label and said second reagent comprises a second oligonucleotide comprising a second label, wherein said first and second oligonucleotides are capable of hybridizing to said target amplicon to form hybridized target amplicons comprising said first and second labels, said third reagent comprises first receptors specific for said first label on said hybridized target amplicon and having colored microparticles bound thereto, and said fourth reagent comprises membrane-bound second receptors specific for said second label on said hybridized target amplicon.

9. The method of claim 7, wherein said amplification methodology is polymerase chain reaction (PCR), ligase chain reaction, Qβ replicase, strand displacement assay (SDA), nucleic acid sequence-based amplification (NASBA), or cascade rolling circle amplification (CRCA).

10. A method of detecting a target nucleic acid in a sample, wherein all of said method steps take place within a multi-chambered self-contained device having at least two chambers, said method comprising:
  a) extracting said target nucleic acid, wherein said extraction includes binding said target nucleic acid to a solid phase or silica slurry;
  b) hybridizing said target nucleic acid to a DNA-RNA-DNA probe having a first label on the 5' end and a second label on the 3' end to form a reaction mixture comprising a hybridized product having a first and second label, wherein prior to hybridization said nucleic acid present in a double-stranded form are rendered single-stranded;
  c) transferring said reaction mixture to a detection chamber of said device; and
  d) detecting said target nucleic acid within said detection chamber by a lateral flow assay, wherein said assay comprises:
    i) contacting said hybridized product with colored microparticles having first receptors bound thereto, wherein said first receptors on said microparticles are specific for and bind to said first label;
    ii) contacting said microparticle-bound hybridized product with RNase H to form a mixture, wherein said RNase H cleaves said probe only if said probe is hybridized to said target nucleic acid; and
    iii) contacting said mixture from step ii) with a membrane having a capture zone, wherein said capture zone comprises second receptors specific for said second label, wherein said mixture wicks along said membrane to said capture zone and a visible line does not form at said capture zone if said target nucleic acid is present in said sample.

11. A method of detecting a target nucleic acid in a sample, comprising:
  i) extracting said target nucleic acid, wherein extraction takes place in a first tube comprising a solid phase matrix that binds said target nucleic acid, said matrix tube being positioned inside a second tube having a closed end and an open end and lid for closing the open end, said second tube further containing a reagent cell positioned within said second tube and over said first tube and containing nucleic acid amplification reagents;
  ii) amplifying said target nucleic acid bound on said solid phase matrix by releasing said amplification reagents comprising a first primer having a first label and a second primer having a second label from said reagent cell into said first tube under conditions that preferentially amplify said target nucleic acid to produce a reaction mixture comprising target amplicons having said first label and said second label, wherein prior to amplification said nucleic acid present in a double-stranded form are rendered single-stranded;
  iii) inserting a result stick comprising a membrane having first and second reagents disposed thereon through a seal in said cap and into said reaction mixture, wherein when said target amplicons bind to both said first and second reagents a visible signal is detected, and wherein said extraction, amplification, and detection occur while said second tube open end is closed by said lid.

12. The method of claim 11, wherein said reagent cell further comprises at least one pouch containing a diluent.

13. The method of claim 11, wherein said first reagent comprises colored microparticles coated with first receptors specific for said first label and said second reagent comprises second receptors specific for said second label.

14. The method of claim 11, wherein said solid phase matrix is aluminum oxide or silica.

15. A method of detecting a target nucleic acid in a sample, wherein all of said method steps take place within a multi-chambered self-contained device having at least two chambers, said method comprising:
  a) extracting said target nucleic acid, wherein said extraction includes binding said target nucleic acid to a solid phase or silica slurry;
  b) amplifying said target nucleic acid on said solid phase or silica slurry with a first primer having a first label and to a second primer under conditions that preferentially amplify said target nucleic acid to produce an amplification reaction mixture comprising singly labeled target amplicons, wherein prior to hybridization said nucleic acid present in a double-stranded form are rendered single-stranded;
  c) transferring said reaction mixture to a detection chamber of said device; and
  d) detecting said target amplicons within said detection chamber by a lateral flow assay, wherein said assay comprises wicking said singly labeled target amplicons onto a membrane, wherein said singly labeled target amplicons bind to at least a first and a second reagent and at least one of said reagents is bound to said membrane, whereby when said at least two reagents are all bound to said target amplicons a visible signal is detected, wherein said amplification and extraction take place within a first chamber of said device that is in fluid communication with said first chamber, or said extraction takes place within a first chamber of said device and said amplification takes place in a second chamber that is in fluid communication with both said first chamber and said detection chamber.

16. The method of claim 15, wherein said first reagent comprises an oligonucleotide having a colored microparticle bound thereto and capable of specifically hybridizing to said target amplicon, and said second reagent comprises a receptor bound to said membrane and specific for said label on said target amplicon.

* * * * *

UNITED STATES PATENT AND TRADEMARK OFFICE
CERTIFICATE OF CORRECTION

PATENT NO. : 6,649,378 B1  Page 1 of 1
DATED : November 18, 2003
INVENTOR(S) : Diane L. Kozwich et al.

It is certified that error appears in the above-identified patent and that said Letters Patent is hereby corrected as shown below:

<u>Column 1,</u>
Line 4, please insert the following paragraph:
-- CONTRACTUAL ORIGIN OF THE INVENTION
This invention was made with United States Government support under cooperative agreement number 70NANB5H1109 awarded by the National Institute of Standards and Technology (NIST). The United States Government has certain rights in the invention. --

Signed and Sealed this

Twentieth Day of April, 2004

JON W. DUDAS
*Acting Director of the United States Patent and Trademark Office*